(12) United States Patent
Tsuyutani et al.

(10) Patent No.: US 12,125,754 B2
(45) Date of Patent: Oct. 22, 2024

(54) SENSOR PACKAGE SUBSTRATE, SENSOR MODULE INCLUDING THE SAME, AND ELECTRONIC COMPONENT EMBEDDED SUBSTRATE

(71) Applicant: TDK CORPORATION, Tokyo (JP)

(72) Inventors: Kazutoshi Tsuyutani, Tokyo (JP); Yoshihiro Suzuki, Tokyo (JP); Akira Motohashi, Tokyo (JP)

(73) Assignee: TDK CORPORATION, Tokyo (JP)

( * ) Notice: Subject to any disclaimer, the term of this patent is extended or adjusted under 35 U.S.C. 154(b) by 0 days.

(21) Appl. No.: 17/894,584

(22) Filed: Aug. 24, 2022

(65) Prior Publication Data

US 2022/0406670 A1    Dec. 22, 2022

Related U.S. Application Data

(63) Continuation of application No. 16/550,995, filed on Aug. 26, 2019, now Pat. No. 11,462,447.

(30) Foreign Application Priority Data

Jul. 13, 2018  (JP) .................................. 2018-133591

(51) Int. Cl.
  *H01L 23/13*    (2006.01)
  *G01H 3/00*     (2006.01)
  (Continued)

(52) U.S. Cl.
  CPC ............... *H01L 23/13* (2013.01); *G01H 3/00* (2013.01); *G01K 13/02* (2013.01); *G01L 9/0041* (2013.01);
  (Continued)

(58) Field of Classification Search
  CPC ...... H01L 23/13; H01L 23/5389; H01L 25/18
  See application file for complete search history.

(56) References Cited

U.S. PATENT DOCUMENTS 6,594,369 B1    7/2003  Une
2009/0175477 A1  7/2009  Suzuki et al.
(Continued)

FOREIGN PATENT DOCUMENTS

JP    2007-248212 A    9/2007
JP    2009-241164 A   10/2009
(Continued)

OTHER PUBLICATIONS

U.S. PTO Non-Final Office Action issued in related U.S. Appl. No. 16/550,995, mailed Jul. 21, 2021.
(Continued)

*Primary Examiner* — Peniel M Gumedzoe
(74) *Attorney, Agent, or Firm* — Rimon P.C.

(57) ABSTRACT

A sensor package substrate disclosed in the present specification has a mounting area in which a sensor chip is mounted and a controller chip connected to the sensor chip. A through hole is formed in the sensor package substrate so as to overlap the mounting area in a plan view and to penetrate the substrate from one surface to the other surface thereof. The mounting area and the controller chip overlap each other in a plan view. According to the present invention, by reducing the thickness of an insulating layer, it is possible not only to reduce the distance of a wiring for the sensor chip and controller chip, but also to reduce the area of the substrate.

16 Claims, 35 Drawing Sheets

(51) Int. Cl.
*G01K 13/02* (2021.01)
*G01L 9/00* (2006.01)
*G01N 33/00* (2006.01)
*H01L 23/538* (2006.01)
*H01L 25/18* (2023.01)

(52) U.S. Cl.
CPC ..... *G01N 33/0027* (2013.01); *H01L 23/5389* (2013.01); *H01L 25/18* (2013.01)

(56) References Cited

U.S. PATENT DOCUMENTS

| | | |
|---|---|---|
| 2012/0068359 A1 | 3/2012 | Mori et al. |
| 2013/0070951 A1 | 3/2013 | Tanaka et al. |
| 2013/0193533 A1 | 8/2013 | Vos et al. |
| 2013/0328211 A1 | 12/2013 | Shimizu et al. |
| 2014/0306299 A1 | 10/2014 | Kasai |
| 2016/0014530 A1 | 1/2016 | Gao |
| 2017/0006368 A1 | 1/2017 | Brioschi et al. |
| 2017/0057808 A1* | 3/2017 | Chang ................ B81B 7/0064 |
| 2017/0313579 A1 | 11/2017 | Ghidoni et al. |
| 2018/0270958 A1 | 9/2018 | Kitagawa et al. |
| 2019/0011392 A1 | 1/2019 | Mou et al. |
| 2020/0185327 A1 | 6/2020 | Tseng et al. |
| 2021/0035874 A1 | 2/2021 | Kudo et al. |

FOREIGN PATENT DOCUMENTS

| | | |
|---|---|---|
| JP | 2010-268412 A | 11/2010 |
| JP | 2013-149792 A | 8/2013 |
| WO | 2017/209296 A1 | 12/2017 |

OTHER PUBLICATIONS

U.S. PTO Final Office Action issued in related U.S. Appl. No. 16/550,995, mailed Mar. 30, 2022.
U.S. PTO Non-Final Office Action issued in related U.S. Appl. No. 16/550,995, mailed Oct. 28, 2020.
U.S. Appl. No. 16/550,995, filed Aug. 26, 2019.

\* cited by examiner

SENSOR PACKAGE SUBSTRATE, SENSOR MODULE INCLUDING THE SAME, AND ELECTRONIC COMPONENT EMBEDDED SUBSTRATE

CROSS-REFERENCE TO RELATED APPLICATIONS

This is a Continuation of U.S. patent application Ser. No. 16/550,995 filed on Aug. 26, 2019, which claims the benefit of Japanese Patent Application No. 2018-133591 filed on Jul. 13, 2018 including the specification, drawings and abstract are incorporated herein by reference in their entirety.

BACKGROUND OF THE INVENTION

Field of the Invention

The present invention relates to a sensor package substrate and a sensor module having the same and, more particularly, to a sensor package substrate for mounting a sensor that detects air vibration, air pressure, air temperature or air composition, and a sensor module having the same. The present invention relates also to an electric component embedded substrate suitable as the sensor package substrate.

Description of Related Art

As a sensor module having a sensor chip such as a temperature sensor, a sensor module described in JP 2013-149792 A is known. The sensor modules described in JP 2013-149792 A is formed as follows: first, a sensor chip and other electronic components are accommodated in a plurality of recessed parts formed in a substrate; then, wirings for connecting the sensor chip and the electronic components are formed; and finally, the surface of the substrate is resin-sealed.

However, in the sensor module described in JP 2013-149792 A, the sensor chip and other electronic components are mounted on the same plane, so that it is difficult to reduce the distance of the wirings connecting the senor chip and the other electronic component, which in turn results in an increase in the substrate area.

SUMMARY

It is therefore an object of the present invention to provide a sensor package substrate allowing a reduction in the distance of the wirings connecting the sensor chip and other electronic components, a sensor module having the sensor package substrate, and an electronic component embedded substrate.

Another object of the present invention is therefore to provide a sensor package substrate allowing a reduction in the substrate area, a sensor module having the sensor package substrate, and an electronic component embedded substrate.

A sensor package substrate according to the present invention is a substrate having a mounting area which is provided on one surface thereof for mounting a sensor chip and an electronic component connected to the sensor chip. A through hole is formed in the sensor package substrate so as to overlap the mounting area in a plan view and to penetrate the substrate from one surface to the other surface thereof. The mounting area and the electronic component overlap each other in a plan view.

A sensor module according to the present invention has the above sensor package substrate and the sensor chip mounted on the mounting area.

According to the present invention, the sensor chip and the electronic component are laid out so as to overlap each other, so that by reducing the thickness of an insulating layer interposed between the sensor chip and the electronic component, it is possible not only to reduce the distance of a wiring for sensor chip and electronic component, but also to reduce the area of the substrate. Further, the sensor chip can detect the physical quantity of a measurement target through the through hole.

In the present invention, the diameter of the through hole may be constant or may be varied in the depth direction. The former structure can be obtained by machining using a drill, and the latter structure can be obtained by blasting, laser processing, or machining using a plurality of drills having different diameters. In the latter case, the through hole may have different diameters between the edge thereof on one surface side and the edge thereof on the other surface side or may have a tapered shape in which the diameter thereof continuously vary in the depth direction.

In the present invention, the planar shape of the through hole may be non-circular. Such a structure can be obtained by blasting or laser processing.

In the present invention, the electronic component may be embedded in the substrate. This eliminates the need to mount the electronic component on the other side of the substrate opposite to the one side thereof on which the sensor chip is mounted, thereby allowing the other side to be brought closer to a mother board, which can enhance the sensitivity of the sensor.

The sensor package substrate according to the present invention may further include a metal film positioned inside the through hole and having an opening smaller in diameter than the through hole. This can prevent electrostatic breakdown of the sensor chip and make dust or the like unlikely to adhere to the sensor chip through the through hole.

In the present invention, the sensor chip may be a sensor that detects air vibration, air pressure, air temperature or air composition. This allows the air vibration, air pressure, air temperature or air composition to be detected through the through hole.

An electronic component embedded substrate according to the present invention is a substrate in which an electronic component is embedded. The electronic component embedded substrate has a through hole formed so as not to overlap the electronic component in a plan view and so as to penetrate the substrate from one surface to the other surface thereof. The through hole is varied in diameter in the depth direction. In this case, the through hole preferably has different diameters between the edge thereof on one surface side and the edge thereof on the other surface side. Alternatively, the through hole may have a tapered shape in which the diameter thereof is continuously varied in the depth direction.

As described above, according to the present invention, in the sensor package substrate, sensor module having the same, and electronic component embedded substrate, it is possible to reduce the distance of a wiring for connecting the sensor chip and the electronic component and to reduce the area of the substrate.

BRIEF DESCRIPTION OF THE DRAWINGS

The above features and advantages of the present invention will be more apparent from the following description of certain preferred embodiments taken in conjunction with the accompanying drawings, in which.

DETAILED DESCRIPTION OF THE EMBODIMENTS

Figure 1:
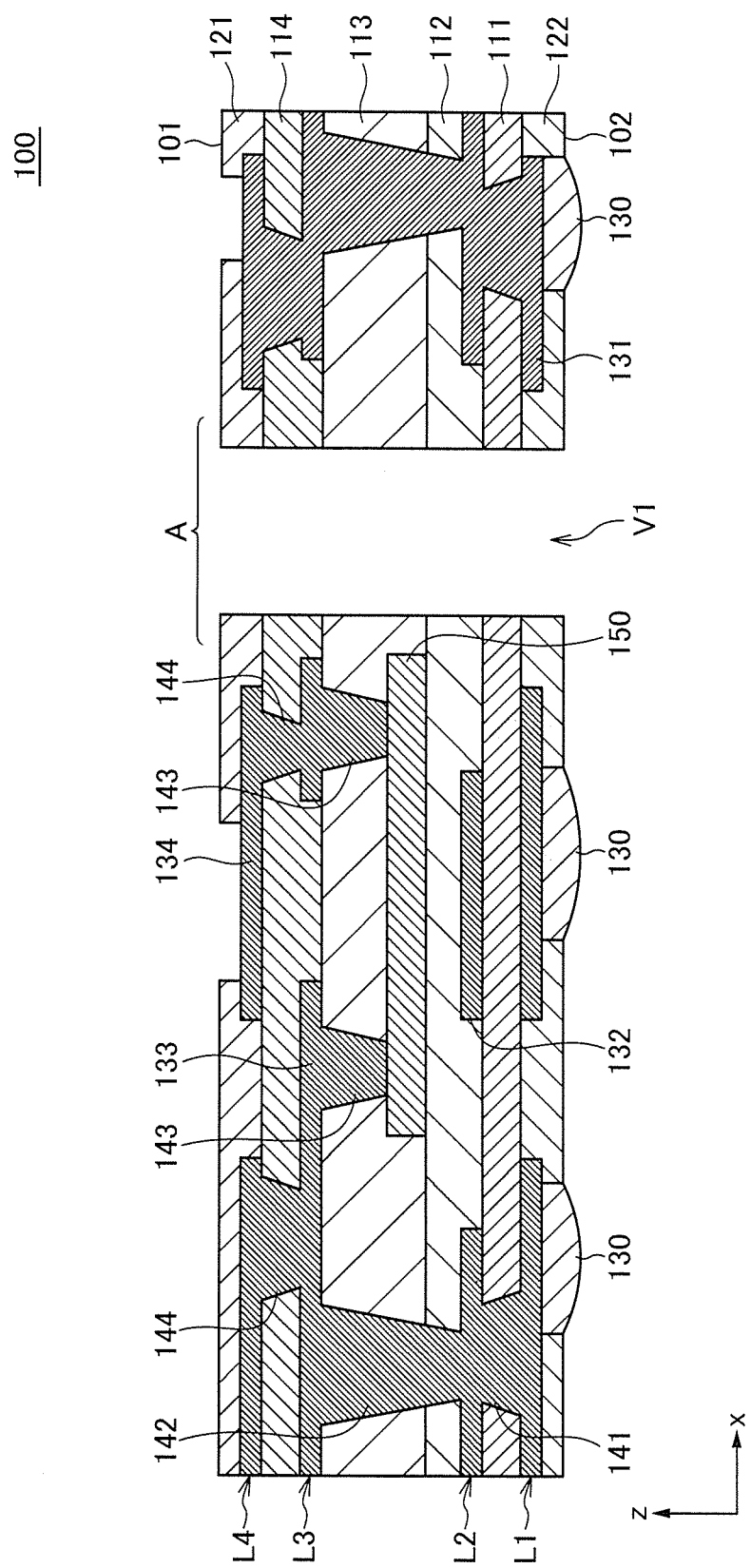
FIG. 1 is a schematic cross-sectional view for explaining the structure of a sensor package substrate 100 according to one embodiment of the present invention.

Hereinafter, preferred embodiments of the present invention will be described in detail with reference to the accompanying drawings. Positional relationships such as upper, lower, left, and right will be based on those in the drawings unless otherwise noted. Further, the dimensional proportions in the drawings are not limited to those illustrated in the drawings. The following embodiments are merely illustrative purposes only, and the invention is not limited to the following embodiments. Further, the present invention can be variously modified without departing from the gist of the invention.

Figure 2:
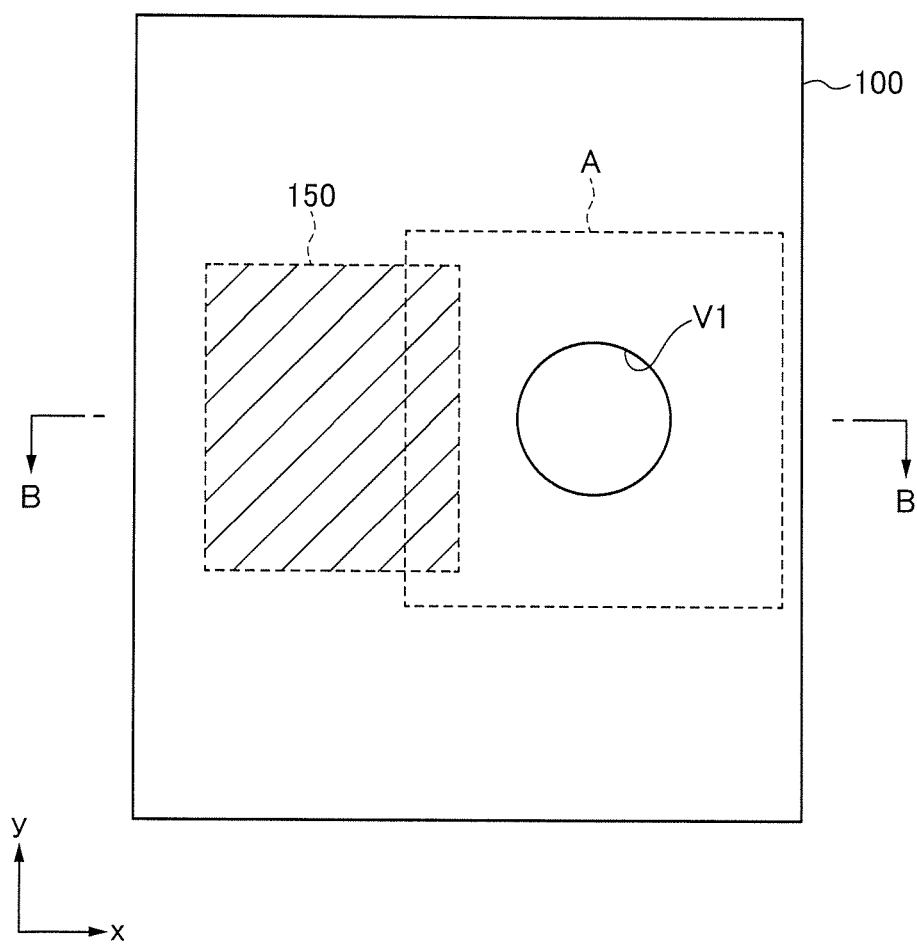
FIG. 2 is a schematic plan view of the sensor package substrate 100.

FIG. 1 is a schematic cross-sectional view for explaining the structure of a sensor package substrate 100 according to one embodiment of the present invention. FIG. 2 is a schematic plan view of the sensor package substrate 100. The cross section illustrated in FIG. 1 is a cross section taken along line B-B in FIG. 2.

As illustrated in FIGS. 1 and 2, the sensor package substrate 100 according to the present embodiment includes four insulating layers 111 to 114 and wiring layers L1 to L4 positioned on the surfaces of the insulating layers 111 to 114. Although not particularly limited, the insulating layer 111 positioned in the lowermost layer and the insulating layer 114 positioned in the uppermost layer may each be a core layer obtained by impregnating a core material such as glass fiber with a resin material such as glass epoxy. On the other hand, the insulating layers 112 and 113 may each be made of a resin material not containing a core material such as glass cloth.

The insulating layer 114 positioned in the uppermost layer and the wiring layer L4 formed on the surface of the insulating layer 114 are partly covered by a solder resist 121. On the other hand, the insulating layer 111 positioned in the lowermost layer and the wiring layer L1 formed on the surface of the insulating layer 111 are partly covered by a solder resist 122. The solder resist 121 constitutes one surface 101 of the sensor package substrate 100, and the solder resist 122 constitutes the other surface 102 of the sensor package substrate 100.

The wiring layers L1 to L4 have wiring patterns 131 to 134, respectively. An external terminal 130 is formed at a part of the wiring pattern 131 that is not covered with the solder resist 122. The external terminal 130 serves as a connection terminal to a motherboard to be described later. A part of the wiring pattern 134 that is not covered with the solder resist 121 is used as a bonding pad. The wiring patterns 131 to 134 are mutually connected through through conductors 141 to 144 penetrating the insulating layers 111 to 114.

In the present embodiment, a mounting area A for a sensor chip is provided on the one surface 101 of the sensor package substrate 100. Further, a through hole V1 penetrating the sensor package substrate 100 from the one surface 101 to the other surface 102 is formed at a position overlapping the mounting area A in a plan view. The through hole V1 is not closed but opened to both the one surface 101 and the other surface 102, allowing air to circulate through the through hole V1.

The sensor package substrate 100 according to the present embodiment has a controller chip 150 which is embedded between the insulating layers 112 and 113. The controller chip 150 is an electronic component connected to a sensor chip mounted in the mounting area A. Naturally, the controller chip 150 is disposed so as to avoid the through hole V1. However, as illustrated in FIG. 2, the controller chip 150 and the mounting area A may partly overlap each other in a plan view. In the present invention, the electronic component such as the controller chip 150 is not particularly limited in type and may be a digital IC having a very high operating frequency (MEMS (Micro Electro Mechanical Systems), a CPU (Central Processing Unit), a DSP (Digital Signal Processor), a GPU (Graphics processing Unit), an ASIC (Application Specific Integrated Circuit), etc.), a memory-based IC (an F-Rom, an SDRAM, etc.), an active element such as an analog IC (an amplifier, an antenna switch, a high-frequency oscillation circuit, etc.), or a passive element (a varistor, a resistor, a capacitor, etc.).

In the present specification, the "sensor package substrate" does not indicate only an individual substrate (individual piece, individual product) which is a unit substrate having an electronic component incorporated therein or mounted thereon but may refer to an aggregate substrate (work board, work sheet) that includes a plurality of the individual substrates.

Figure 3:
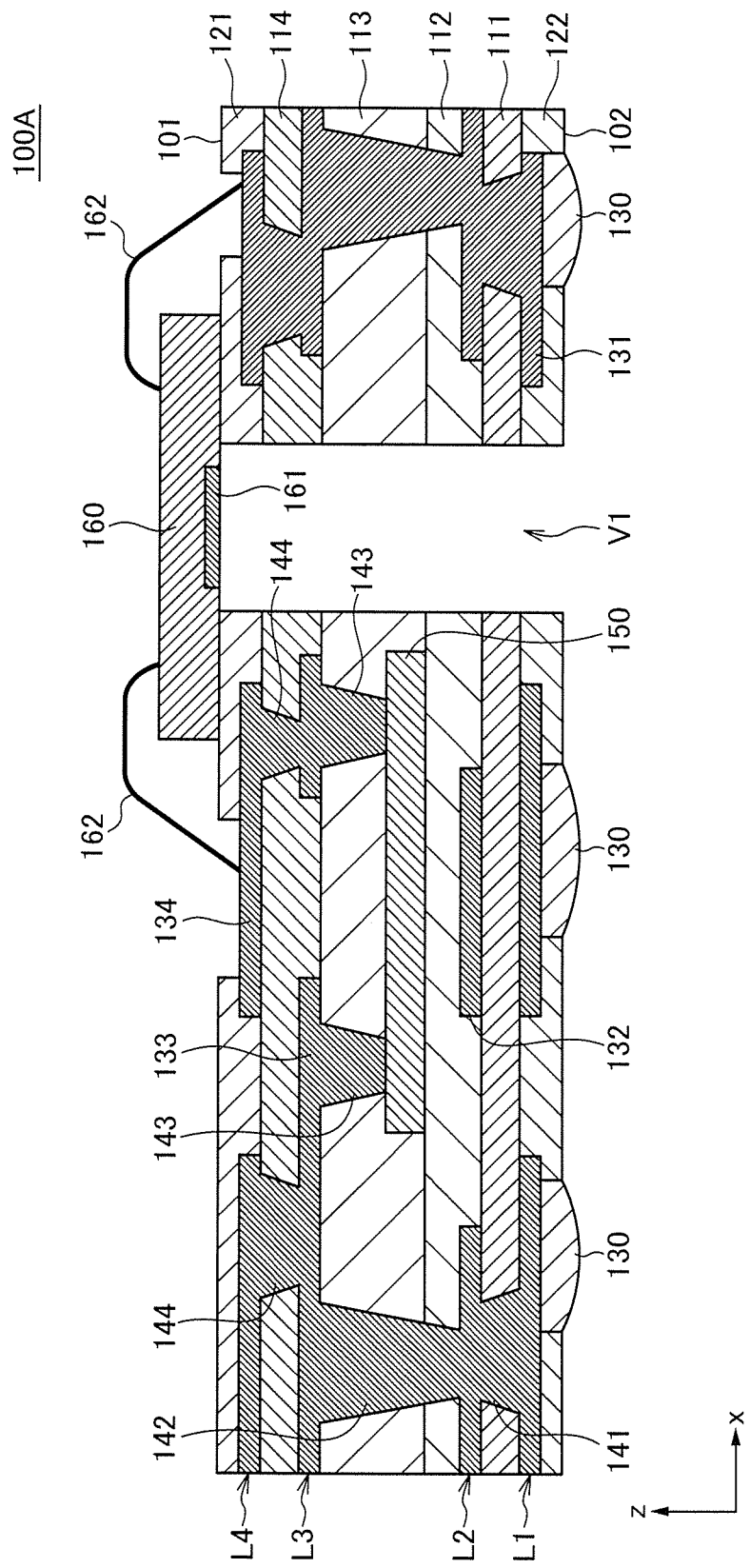
FIG. 3 is a schematic cross-sectional view for explaining the structure of a sensor module 100A.
Figure 4:
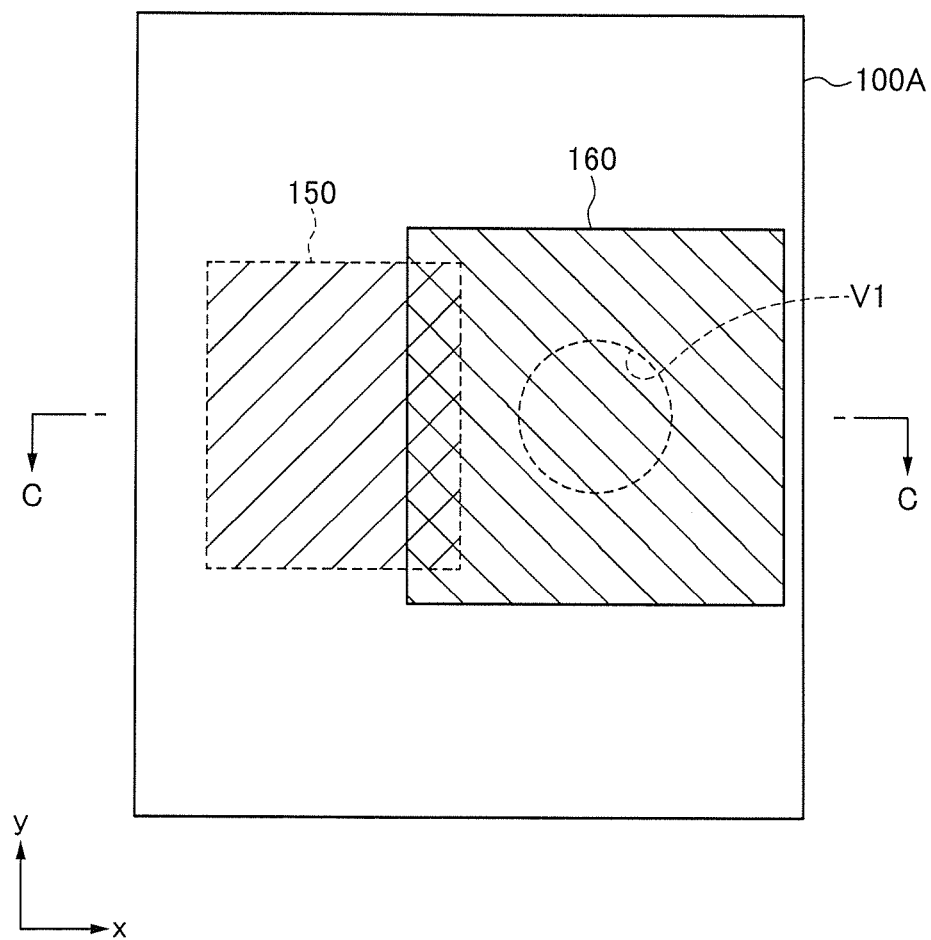
FIG. 4 is a schematic plan view of the sensor module 100A.

FIG. 3 is a schematic cross-sectional view for explaining the structure of a sensor module 100A using the sensor package substrate 100. FIG. 4 is a schematic plan view of the sensor module 100A. The cross section illustrated in FIG. 3 is a cross section taken along line C-C in FIG. 4.

As illustrated in FIGS. 3 and 4, in the sensor module 100A according to the present embodiment, a sensor chip 160 is mounted in the mounting area A of the sensor package substrate 100. The sensor chip 160 is a sensor for detecting, e.g., air vibration, air pressure, air temperature or air composition, i.e., a microphone, a pressure sensor, a temperature sensor, a gas sensor or the like. A detection part 161 of the sensor chip 160 is provided at a position facing the surface 101 of the sensor package substrate 100. At least part of the detection part 161 is exposed to the through hole V1. Thus, the detection part 161 of the sensor chip 160 is exposed to atmosphere through the through hole V1 and can thus detect air vibration, air pressure, air temperature or air composition. An output signal from the detection part 161 is connected to the wiring pattern 134 through a bonding wire 162. However, the method for connecting the sensor package substrate 100 and the sensor chip 160 is not limited to this, but flip-chip connection may be used.

Figure 5:
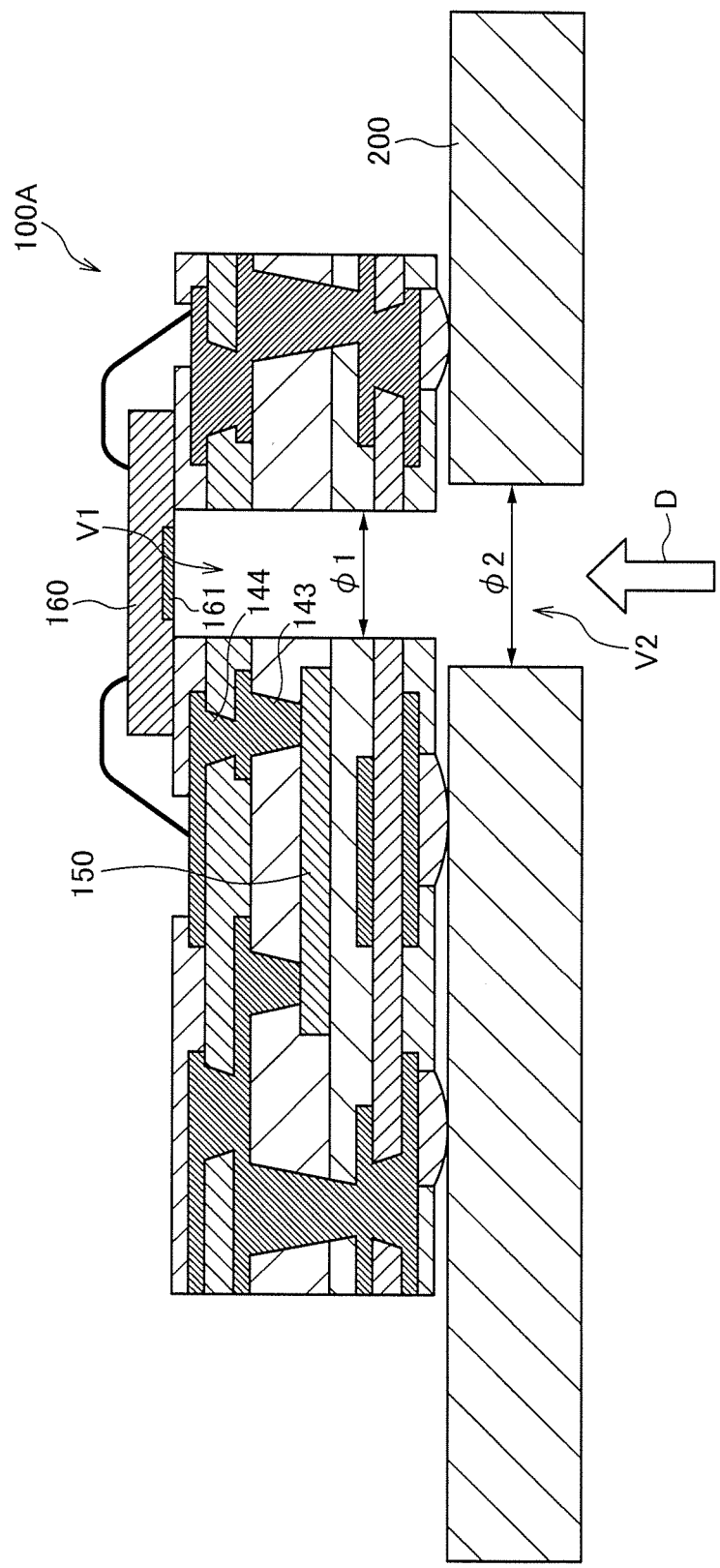
FIG. 5 is a schematic cross-sectional view illustrating a state where the sensor module 100A is mounted on a motherboard 200.

FIG. 5 is a schematic cross-sectional view illustrating a state where the sensor module 100A according to the present embodiment is mounted on a motherboard 200.

As illustrated in FIG. 5, a through hole V2 is formed in the motherboard 200, and the sensor module 100A is mounted on the motherboard 200 such that the through hole V1 and through hole V2 overlap each other in a plan view. Thus, the detection part 161 of the sensor chip 160 is exposed to atmosphere through the through holes V1 and V2. As a result, as dented by arrow D, air vibration, air pressure, air temperature or air composition is transmitted to the sensor chip 160, allowing the physical quantity thereof to be detected. Further, in the present embodiment, electronic component and the like are not mounted on the back surface of the sensor module 100A, so that it is possible to make a gap between the sensor module 100A and the motherboard 200 very small. This can enhance the sensitivity of the sensor. The gap between the sensor module 100A and the motherboard 200 may be filled with an underfill. In the example illustrated in FIG. 5, a diameter ϕ2 of the through hole V2 is slightly larger than a diameter ϕ1 of the through hole V1; however, this is not essential in the present invention. Thus, the diameter ϕ2 of the through hole V2 may be smaller than the diameter ϕ1 of the through hole V1, or the diameter ϕ1 of the through hole V1 and the diameter ϕ2 of the through hole V2 may be substantially equal to each other.

The following describes a manufacturing method for the sensor package substrate 100 according to the present embodiment.

FIGS. 6 to 13 are process views for explaining the manufacturing method for the sensor package substrate 100 according to the present embodiment.

Figure 6:
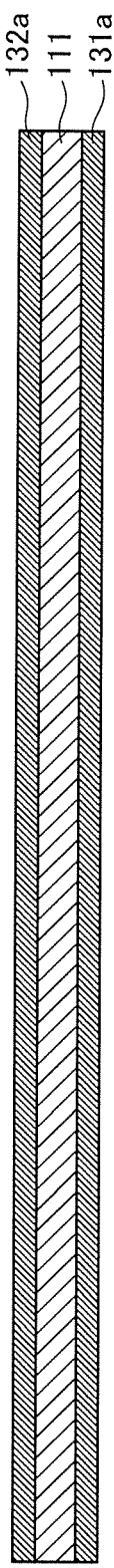
FIGS. 6 to 13 are process views for explaining the manufacturing method for the sensor package substrate 100.

As illustrated in FIG. 6, a base material (a work board) formed by attaching metal films 131a and 132a such as Cu foils to both surfaces of the insulating layer 111 including a core material such as glass fiber, i.e., a double-sided CCL (Copper Clad Laminate) is prepared. In order to facilitate the formation of the through hole V1 in the subsequent process and to ensure appropriate rigidity for easy handling, the thickness of the core material included in the insulating layer 111 is preferably equal to or less than 40 μm. The material forming the metal films 131a and 132a is not particularly limited, and examples thereof include metal conductive materials such as Au, Ag, Ni, Pd, Sn, Cr, Al, W, Fe, Ti and SUS in addition to above-mentioned Cu and, among them, Cu is preferable in terms of conductivity and cost. The same is applied to other metal films to be described later.

The resin material forming the insulating layer 111 is not particularly limited as long as it can be formed into a sheet shape or a film shape, and examples include: a single element selected from the group consisting of vinyl benzyl resin, polyvinyl benzyl ether compound resin, bismaleimide triazine resin (BT resin), polyphenylene ether (polyphenylene ether oxide) resin (PPE, PPO), cyanate ester resin, epoxy+activated ester curing resin, polyphenylene ether resin (polyphenylene oxide resin), curable polyolefin resin, benzo cyclobutene resin, polyimide resin, aromatic polyester resin, aromatic liquid crystal polyester resin, polyphenylene sulfide resin, polyether imide resin, polyacrylate resin, polyetheretherketone resin, fluororesin, epoxy resin, phenolic resin, and benzoxazine resin in addition to glass epoxy; a material obtained by adding, to one of the above-listed resins, silica, talc, calcium carbonate, magnesium carbonate, aluminum hydroxide, magnesium hydroxide, aluminum borate whiskers, potassium titanate fiber, alumina, glass flakes, glass fiber, tantalum nitride, aluminum nitride, or the like; and a material obtained by adding, to one of the above-listed resins, metal oxide powder containing at least one metal selected from the group consisting of magnesium, silicon, titanium, zinc, calcium, strontium, zirconium, tin, neodymium, samarium, aluminum, bismuth, lead, lanthanum, lithium and tantalum, and these examples may be selectively used as appropriate from the viewpoints of electrical characteristics, mechanical characteristics, water absorption properties, reflow durability, etc. Further, examples of the core material included in the insulating layer 111 include a material blended with, e.g., resin fiber such as glass fiber or aramid fiber.

Figure 7:
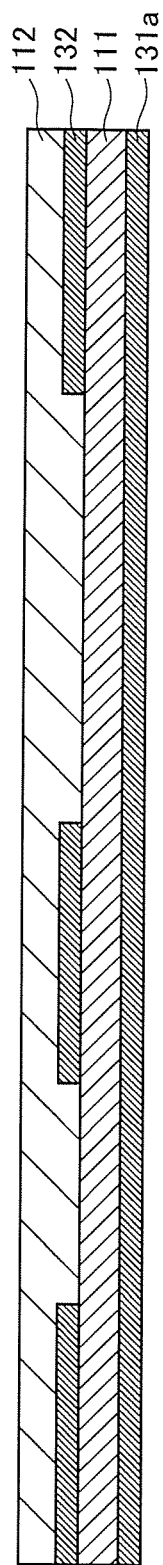

Next, as illustrated in FIG. 7, a known method such as photolithography is used to pattern the metal film 132a to form the wiring pattern 132. Further, for example, an uncured (B stage) resin sheet is laminated on the surface of the insulating layer 111 by vacuum pressure bonding or the like so as to embed therein the wiring pattern 132 to thereby form the insulating layer 112.

Figure 8:
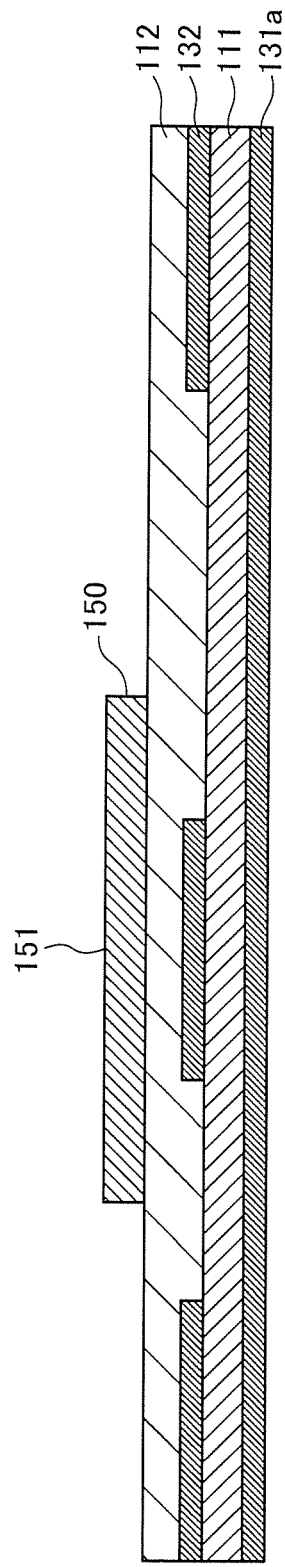

Then, as illustrated in FIG. 8, the controller chip 150 is placed on the insulating layer 112. The controller chip 150 is, e.g., a bare chip semiconductor IC and is face-up mounted such that a substantially rectangular plate-like main surface 151 faces upward. Not-shown many external terminals are provided on the main surface 151 of the controller chip 150. The controller chip 150 is polished at its back surface and thus has a thickness smaller than that of ordinary semiconductor ICs. Specifically, the thickness of the controller chip 150 is, e.g., equal to or less than 200 µm, preferably, about 50 µm to about 100 µm. In terms of cost, it is preferable to simultaneously apply machining to many controller chips 150 in a wafer state and, in this case, the back surface is first ground, and then the wafer is diced to obtain individual controller chips 150. Alternatively, when the wafer is diced into individual controller chips 150 or half-cut before thinning by means of polishing, the back surface can be polished while the main surface 151 of the controller chip 150 is covered with a thermosetting resin or the like. Thus, the process order among insulating film grinding, electronic component back surface grinding and dicing can be varied. The back surface of the controller chip 150 can be roughened by etching, plasma processing, laser processing, blasting, polishing with a grinder, buffing, chemical treatment or the like. With these methods, it is possible to not only achieve thinning of the controller chip 150, but also to enhance adhesion to the insulating layer 112.

Figure 9:
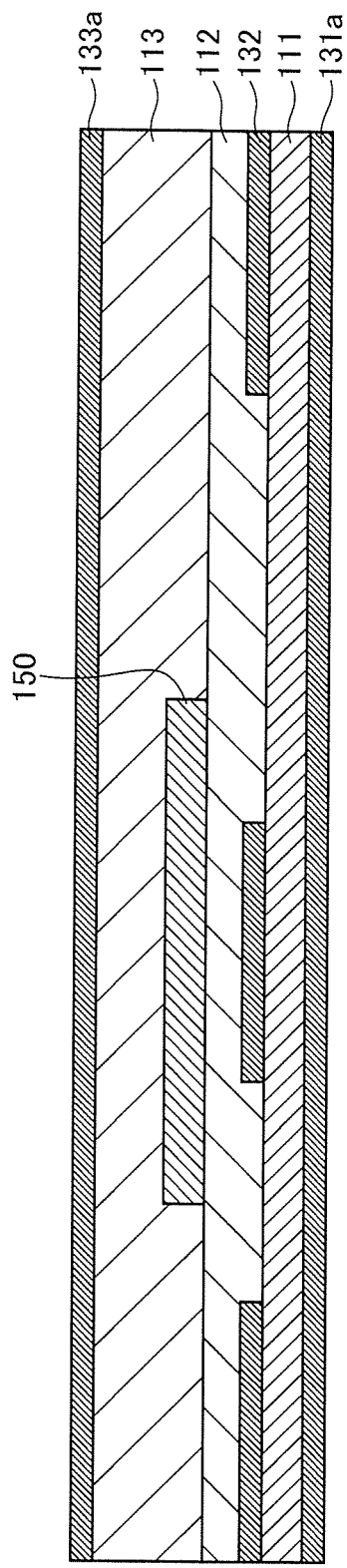

Then, as illustrated in FIG. 9, the insulating layer 113 and a metal film 133a are formed so as to cover the controller chip 150. Preferably, the insulating layer 113 is formed as follows: after application of an uncured or semi-cured thermosetting resin, the resin (when it is uncured resin) is semi-cured by heating, and then the semi-cured resin and metal film 133a are pressed together by a pressing means to obtain a cured insulating layer 113. The insulating layer 113 is preferably a resin sheet not containing fiber that prevents embedding of the controller chip 150. This enhances adhesion among the insulating layer 113, metal film 133a, insulating layer 112 and controller chip 150.

Figure 10:
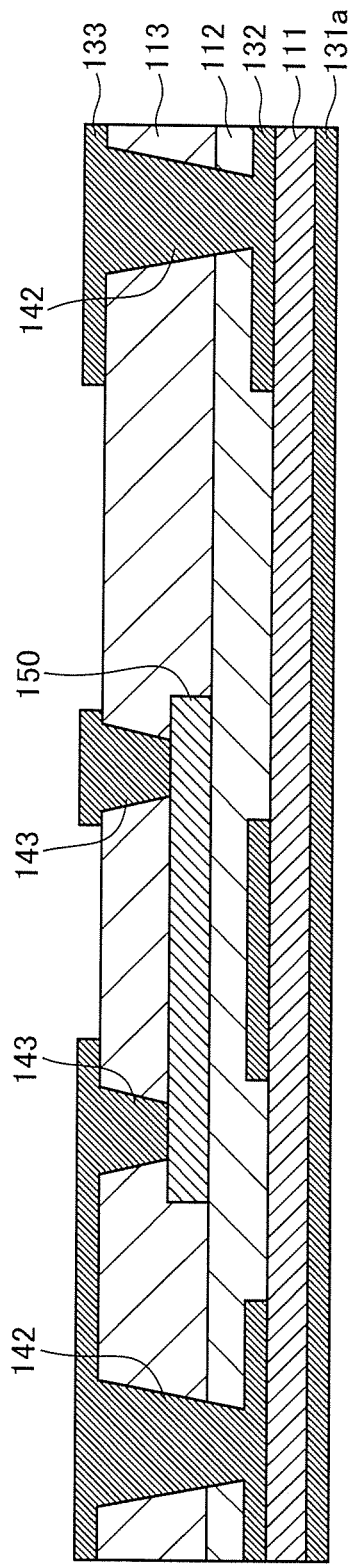

Then, as illustrated in FIG. 10, part of the metal film 133a is etching-removed by using a known method such as photolithography, and then known blasting or laser processing is applied to a predetermined position where the metal film 133a is removed to form through holes in the insulating layers 112 and 113. After that, electroless plating and electrolytic plating are applied, followed by patterning of the metal film 133a by a known method, to thereby form the wiring pattern 133 and through hole conductors 142 and 143. The through hole conductor 142 penetrates the insulating layers 113 and 112 to connect the wiring patterns 132 and 133, and the through hole conductor 143 penetrates the insulating layer 113 to connect the wiring pattern 133 and the controller chip 150.

Figure 11:
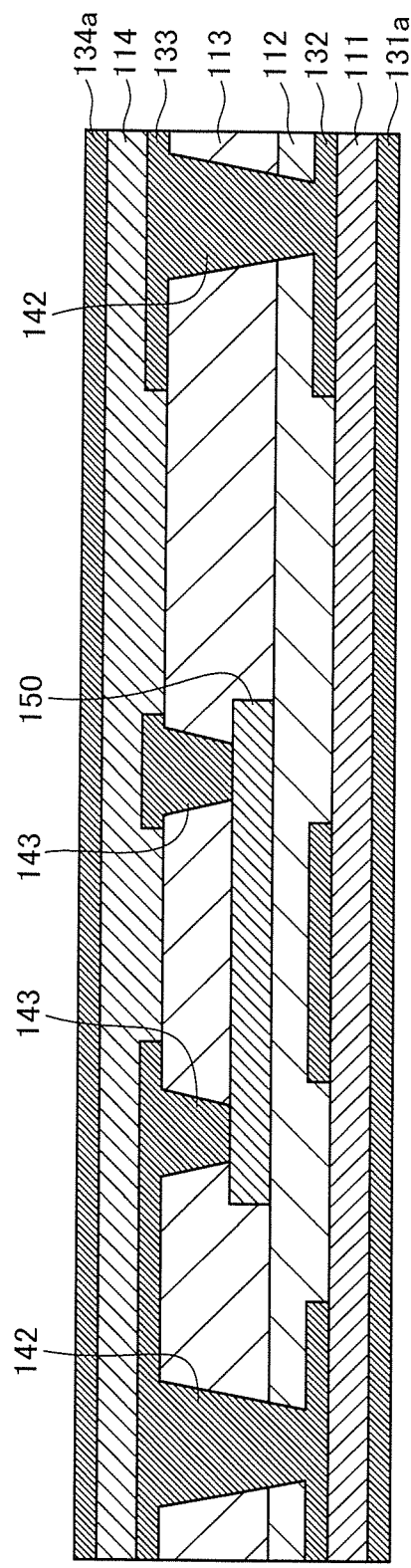

Then, as illustrated in FIG. 11, a sheet having the insulating layer 114 and a metal film 134a laminated thereon is hot-pressed under vacuum so as to embed therein the wiring pattern 133. The material and thickness of the insulating layer 114 may be the same as those of the insulating layer 111.

Figure 12:
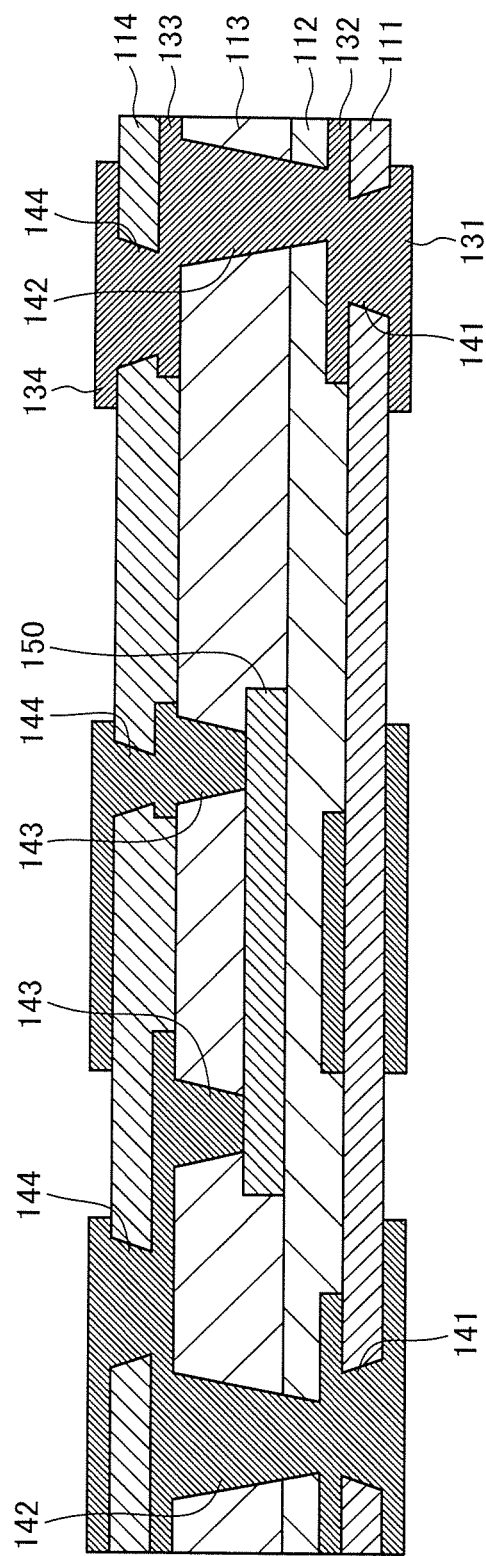

Then, as illustrated in FIG. 12, part of the metal film 131a and part of the metal film 134a are etched away by using a known method such as photolithography, and then known blasting or laser processing is applied to predetermined positions where the metal films 131a and 134a has been removed to form through holes in the insulating layers 111 and 114. After that, electroless plating and electrolytic plating are applied to form through hole conductors 141 and 144, and the metal films 131a and 134a are patterned using a known method, to thereby form the wiring patterns 131 and 134 and through hole conductors 141 and 144. The through hole conductor 141 penetrates the insulating layer 111 to connect the wiring patterns 131 and 132, and the through hole conductor 144 penetrates the insulating layer 114 to connect the wiring patterns 133 and 134.

Figure 13:
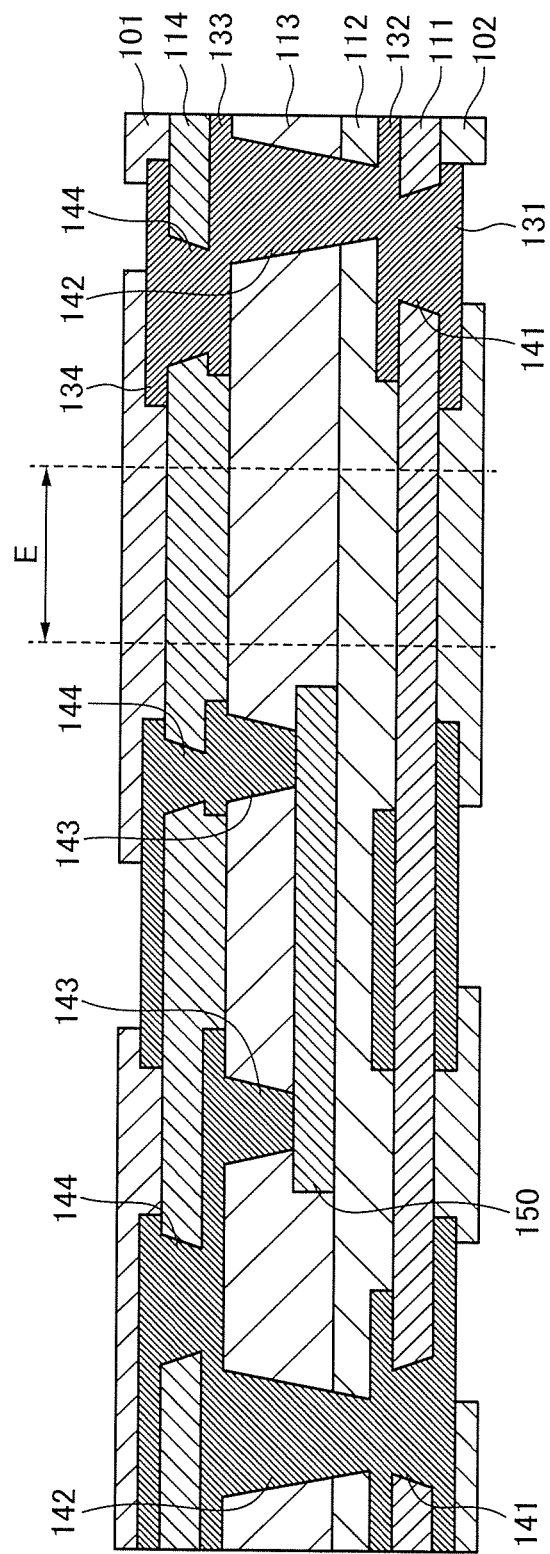

Then, as illustrated in FIG. 13, the solder resists 121 and 122 are formed on the surfaces of the insulating layers 114 and 111, respectively, and surface treatment for component mounting is applied at positions where the wiring patterns 134 and 131 are exposed respectively through the solder resists 121 and 122. The surface treatment may be Cu—OSP, Ni/Au plating, ENEPIG and solder lever treatment, but not limited thereto as long as it aims to prevent oxidation of the wiring pattern and to improve quality in component mounting in the subsequent process.

Then, drilling is applied to the range E in FIG. 13 to form the through hole V1 illustrated in FIG. 1, whereby the sensor package substrate 100 according to the present embodiment is completed. Further, the sensor chip 160 is mounted on the sensor package substrate 100, whereby the sensor module 100A illustrated in FIG. 3 is completed. Formation of the through hole V1 need not be performed in the final process, and may be at any timing as long as it is after the process illustrated in FIG. 11. Further, when a metal film is formed on the inner wall of the through hole V1 by plating, it is possible to improve acoustic characteristics.

The diameter $\phi 1$ of the through hole V1 may be constant or may vary in the depth direction.

Figure 14:
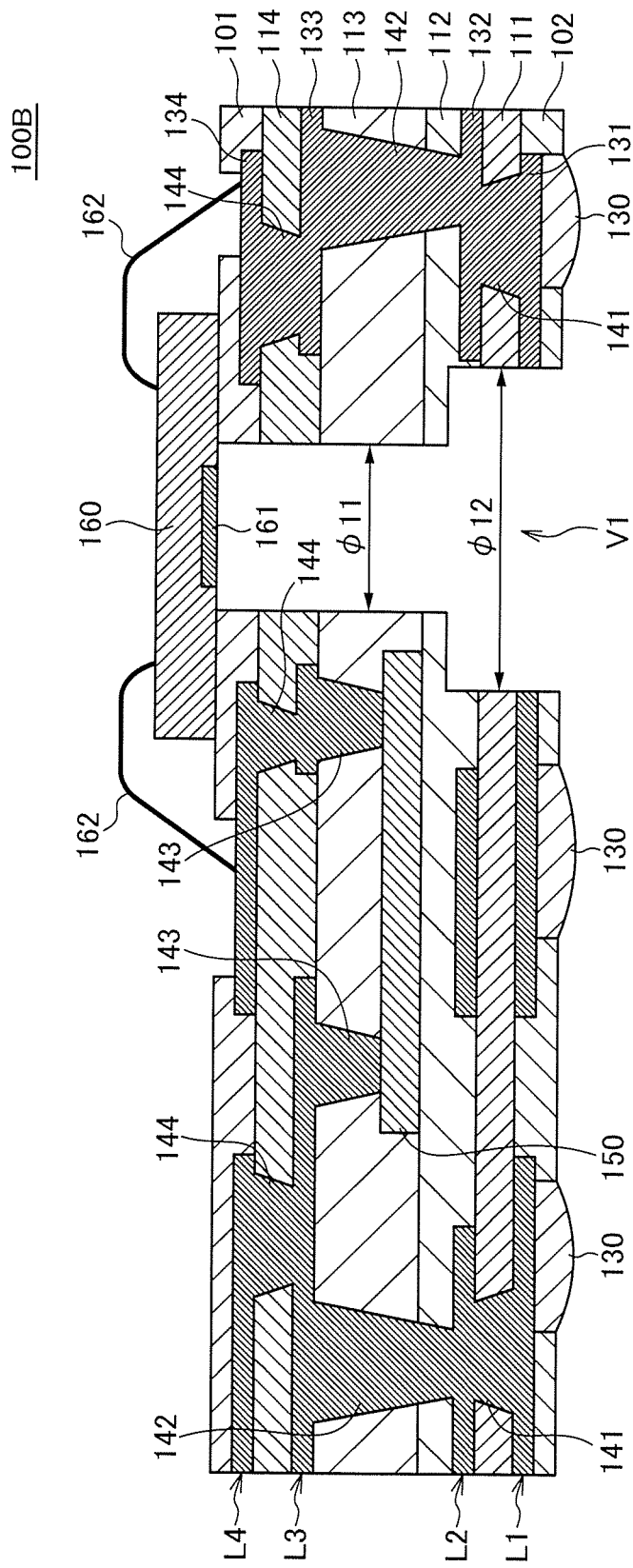
FIG. 14 is a schematic cross-sectional view for explaining the structure of a sensor module 100B according to a first modification.

For example, as in a sensor module 100B according to the first modification illustrated in FIG. 14, the diameter of the through hole V1 may be increased on the other surface 102 side. That is, a diameter $\phi 12$ of the through hole V1 on the other surface 102 side facing the motherboard 200 may be larger than a diameter $\phi 11$ thereof on the one surface 101 side on which the sensor chip 160 is to be mounted. Such a structure can be obtained by drilling, using two drills having different diameters, from the front and back sides. With such a structure of the through hole V1, even when a misalignment occurs at the time of mounting the sensor module 100B on the motherboard 200, it is possible to ensure overlap between the through hole V1 of the sensor module 100B and through hole V2 of the motherboard 200 and to achieve high-density mounting of the sensor chip 160. In the example of FIG. 14, the controller chip 150 and the diameter-increased part of the through hole V1 overlap each other. By thus forming the diameter-increased part in the through hole V1, avoiding the depth position corresponding to the controller chip 150, it is possible to make the controller chip 150 and the through hole V1 partially overlap each other.

Figure 15:
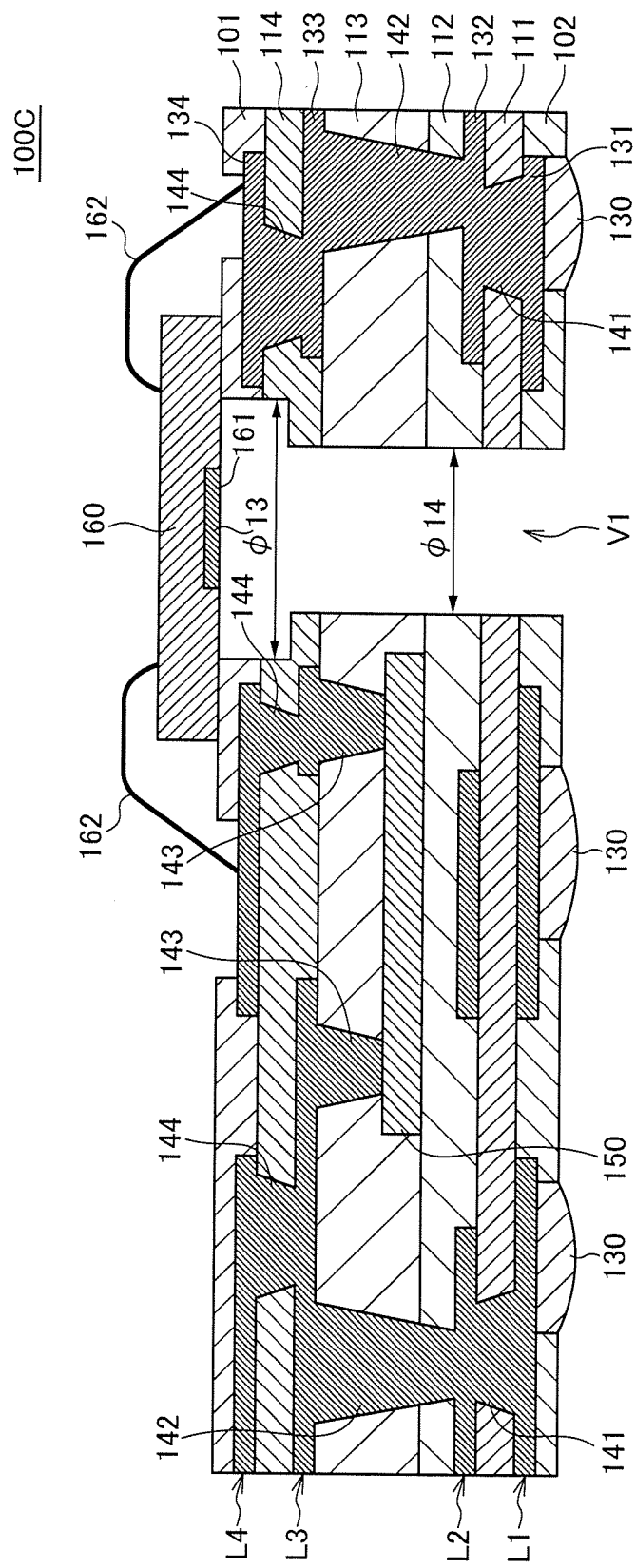
FIG. 15 is a schematic cross-sectional view for explaining the structure of a sensor module 100C according to a second modification.

Alternatively, as in a sensor module 100C according to the second modification illustrated in FIG. 15, the diameter of the through hole V1 may be increased on the one surface 101 side. That is, a diameter $\phi 3$ of the through hole V1 on the one surface 101 side on which the sensor chip 160 is to be mounted may be larger than a diameter $\phi 4$ thereof on the other surface 102 side facing the motherboard 200. Such a structure can also be obtained by drilling, using two drills having different diameters, from the front and back sides. With such a structure of the through hole V1, it is possible to sufficiently ensure the diameter of the through hole V1 for the detection part 161 of the sensor chip 160 while sufficiently ensuring a margin between the controller chip 150 and through hole V1. Even in this example, the controller chip 150 and the diameter-increased part of the through hole V1 may overlap each other.

Figure 16:
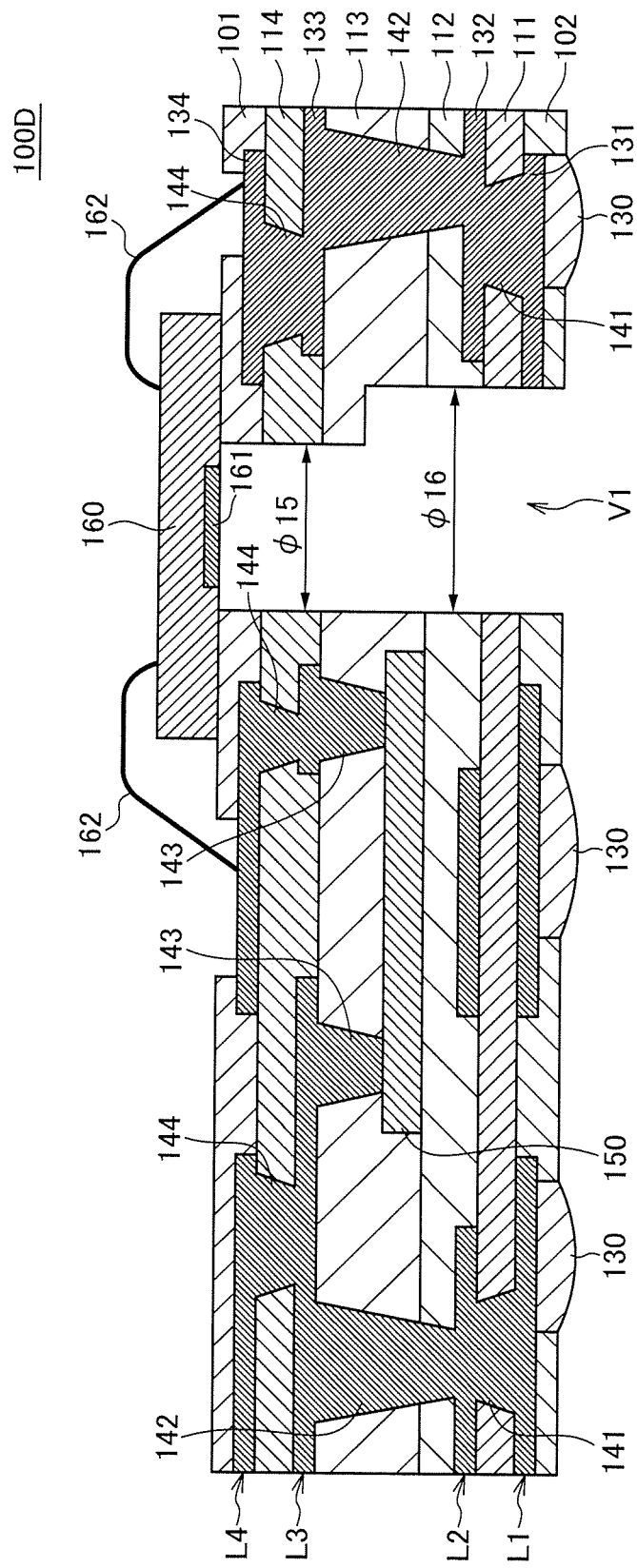
FIG. 16 is a schematic cross-sectional view for explaining the structure of a sensor module 100D according to a third modification.
Figure 17:
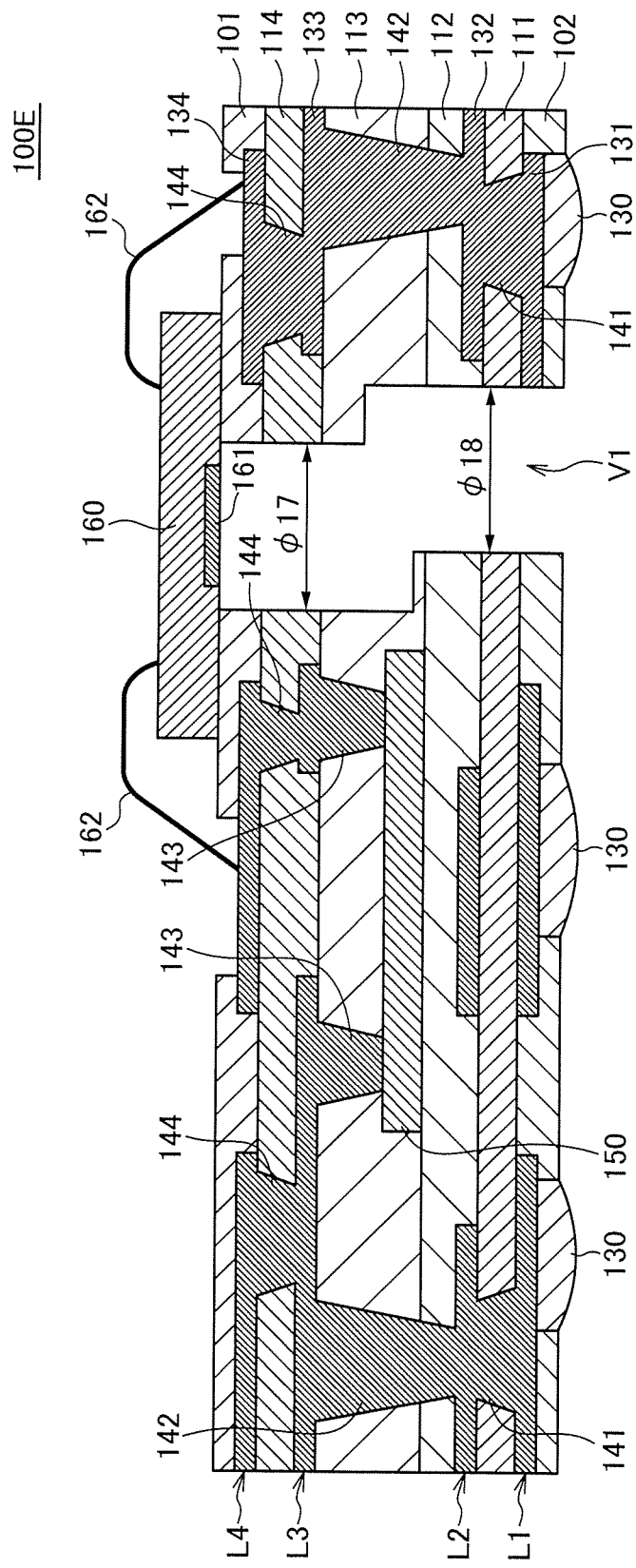
FIG. 17 is a schematic cross-sectional view for explaining the structure of a sensor module 100E according to a fourth modification.

Further, as in a sensor module 100D according to the third modification illustrated in FIG. 16, a diameter φ15 of the through hole V1 on the one surface 101 side and a diameter φ16 thereof on the other surface 102 side may differ from each other, and the center axes of the part of the through hole V1 having the diameter φ15 and the part thereof having the diameter φ16 may be displaced from each other. Further, as in a sensor module 100E according to the fourth modification illustrated in FIG. 17, a diameter φ17 of the through hole V1 on the one surface 101 side and a diameter φ18 thereof on the other surface 102 side may be the same, and the center axes of the part of the through hole V1 having the diameter φ17 and the part thereof having the diameter φ18 may be displaced from each other. With the above configurations, a sensing hole path with a high degree of freedom in design can be formed by utilizing a free space of wiring, contributing to further size reduction. Thus, the through hole V1 may be formed into various shapes according to the purpose and conditions.

The through hole V1 may not necessarily be formed by drilling, but may be formed by laser processing using $CO_2$ gas laser or UV laser, or blasting (sand blasting, wet blasting, etc.).

Figure 18:
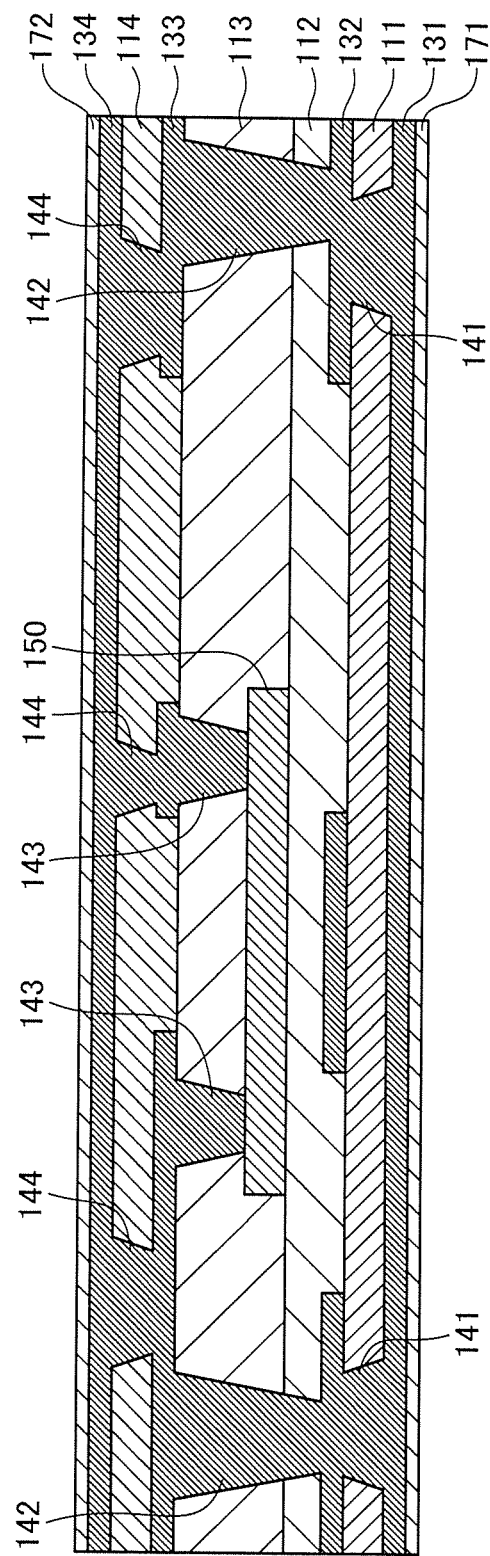
FIGS. 18 to 22 are process views for explaining a method of forming the through hole V1 using laser processing or blasting.
Figure 19:
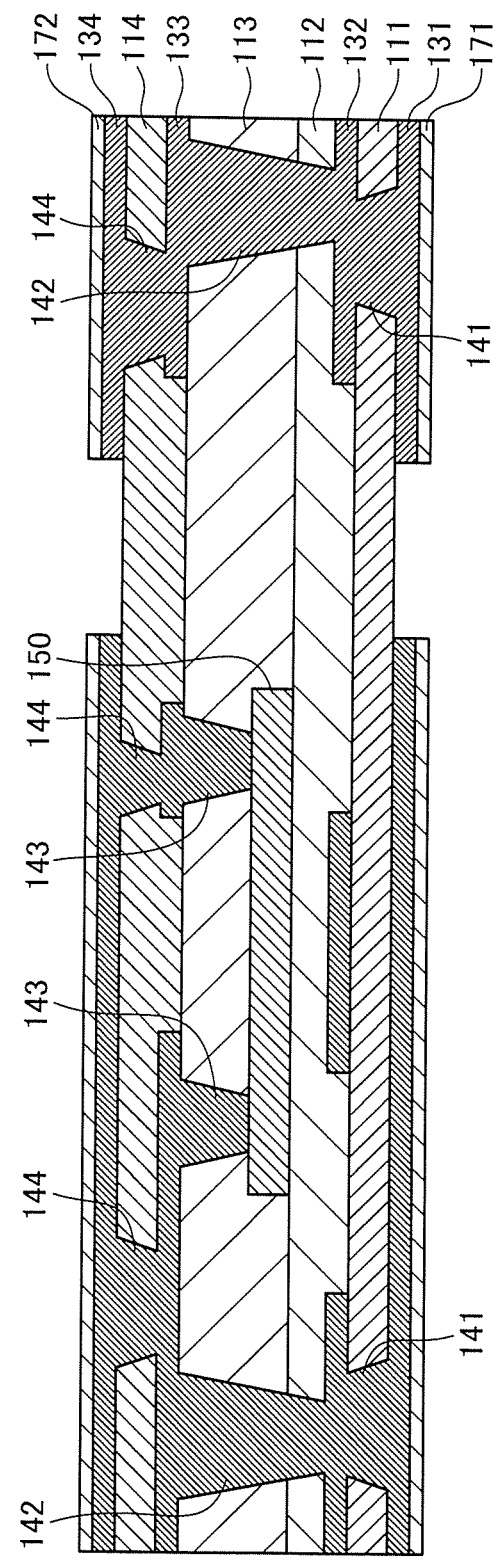
Figure 20:
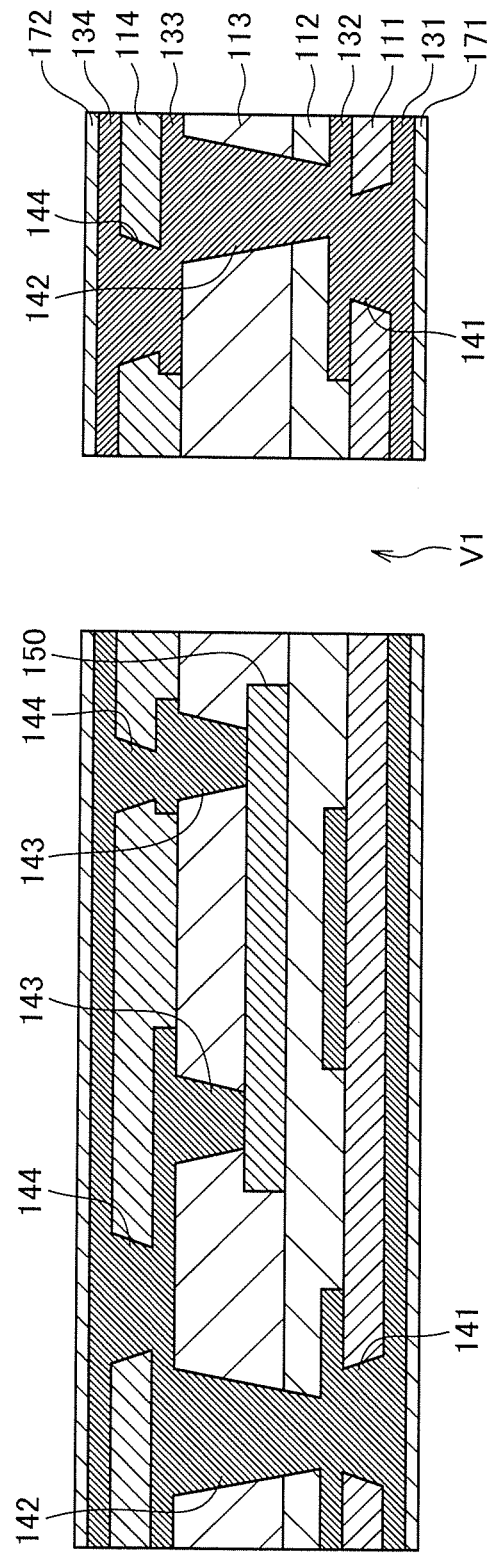

FIGS. 18 to 20 are process views for explaining a method of forming the through hole V1 using laser processing or blasting.

After completion of the processes described using FIGS. 6 to 11, photosensitive dry films 171 and 172 are formed on the surfaces of the metal films 131a and 134a, respectively, as illustrated in FIG. 18. Then, as illustrated in FIG. 19, the dry films 171 and 172 at a planar position where the through hole V1 is to be formed by photolithography are removed, and the metal films 131a and 134a exposed respectively through the dry films 171 and 172 are removed. In this state, as illustrated in FIG. 20, laser processing or blasting is applied to the front and back sides to form the through hole V1 penetrating the insulating layers 111 to 114. In addition, burrs or substrate cracks that can occur during drilling work are not caused, so that product reliability can be enhanced. Further, the positional accuracy of the through hole V1 is determined by alignment of the dry films 171 and 172 in photolithography process, so that it is possible to improve the positional accuracy by one or more orders of magnitude as compared with a pin alignment method which is adopted in drilling work. Furthermore, when the through hole V1 is formed by blasting, many through holes V1 can be formed simultaneously in the form of an assembly substrate, allowing reduction in manufacturing cost. Furthermore, unlike laser processing, improvement in characteristics and quality can be achieved due to smear removal or remaining and dropping of glass fiber.

Figure 21:
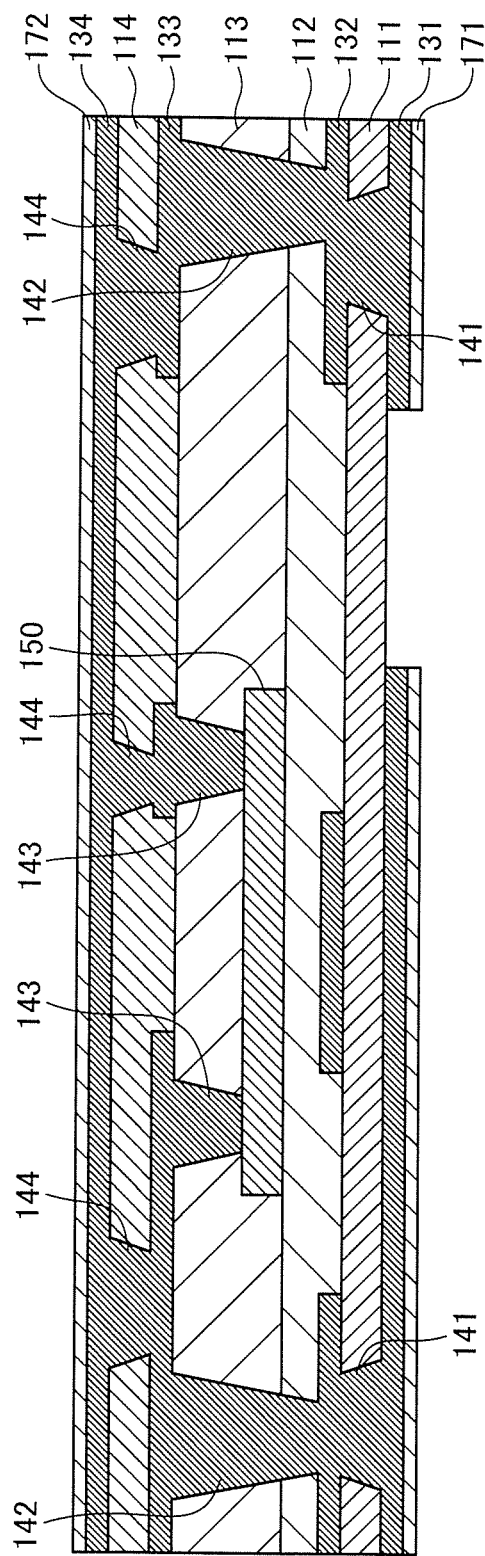
Figure 22:
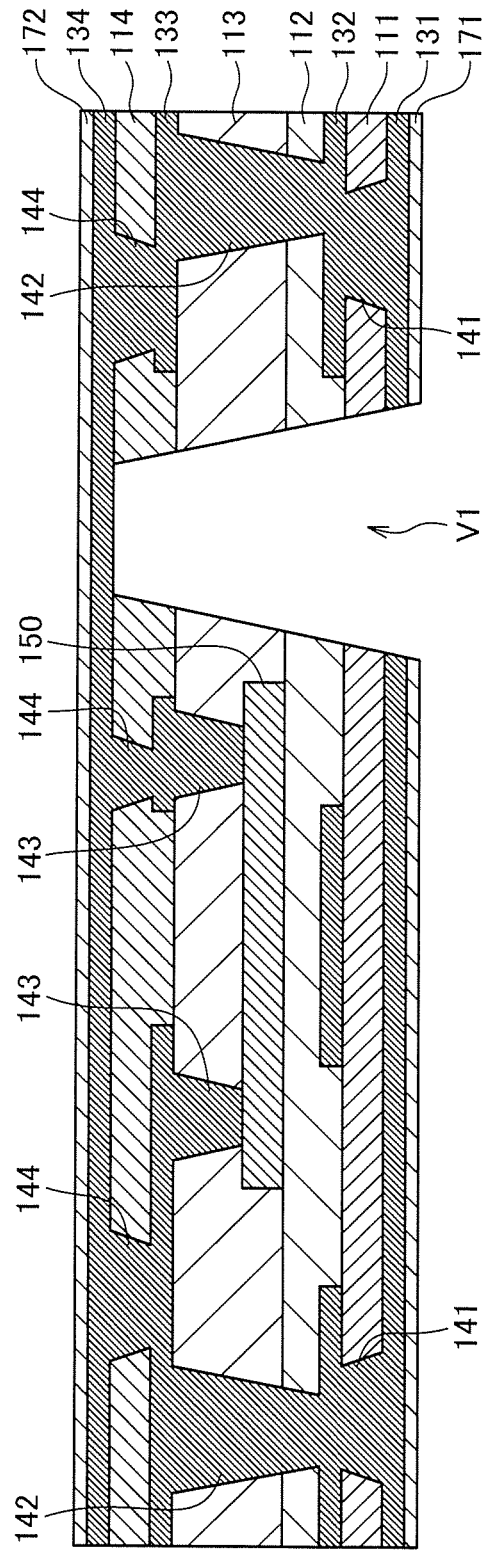
Figure 23:
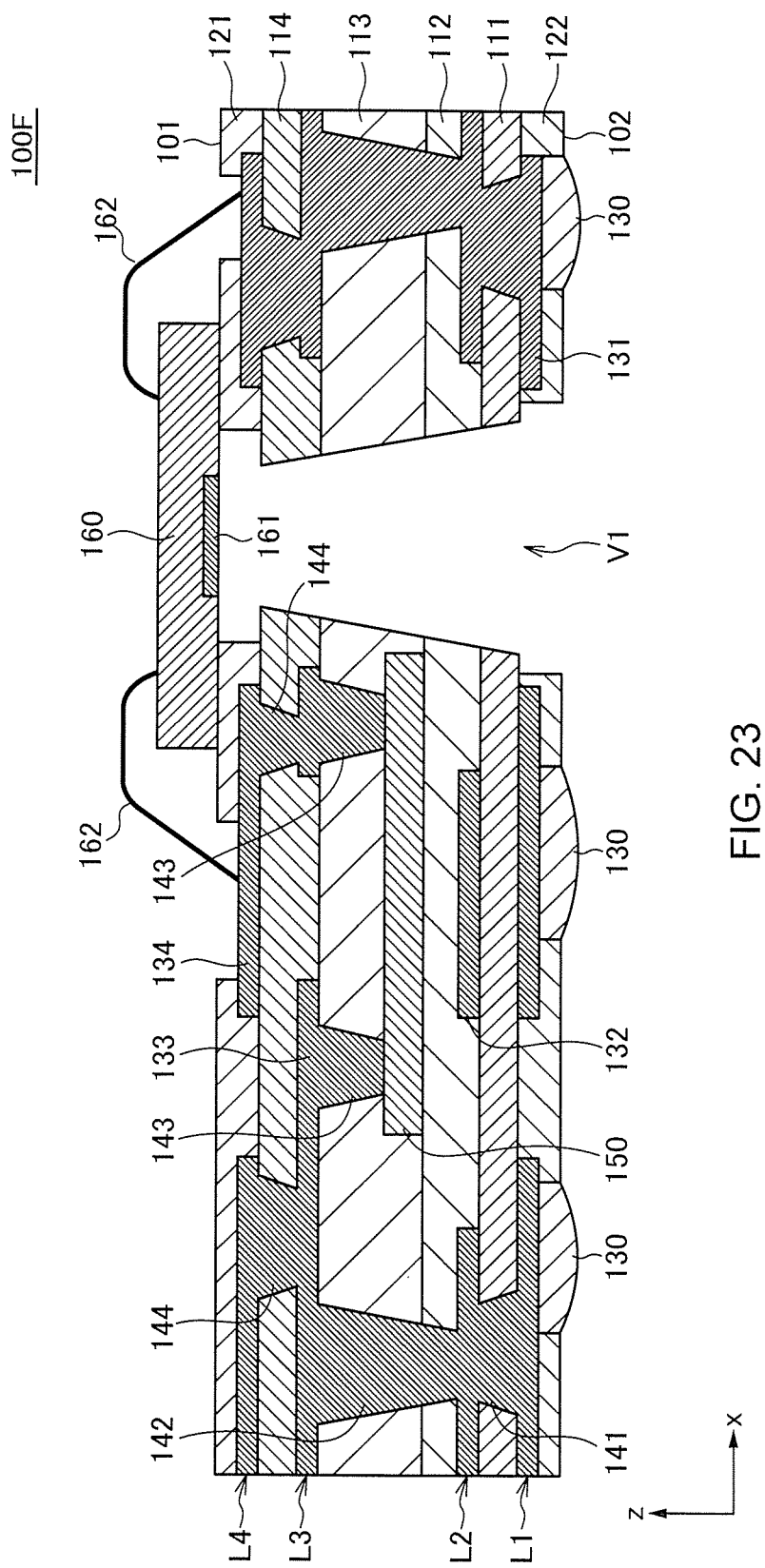
FIG. 23 is a schematic cross-sectional view for explaining the structure of a sensor module 100F according to a fifth modification.

Although laser processing or blasting is applied to the front and back sides in the example illustrated in FIGS. 18 to 20, it may be applied to only the surface 101 side or the other surface 102 side. For example, the through hole V1 may be formed in such a manner as illustrated in FIG. 21. That is, the dry film 172 is not removed, but the dry film 171 at a planar position where the through hole V1 is to be formed is removed, and part of the metal film 131a that is exposed through the dry film 171 is removed. Thereafter, as illustrated in FIG. 22, laser processing or blasting is applied to the other surface 102 side to thereby form the through hole V1 so as to penetrate the insulating layers 111 to 114. In this case, the through hole V1 can be made to have a tapered shape in which the diameter thereof continuously varies in the depth direction depending on laser irradiation conditions or blasting conditions. This is because laser processing or blasting has characteristics in which a machining amount is reduced in the depth direction from the machining surface side. In the example illustrated in FIG. 22, the diameter of the through hole V1 is continuously increased from the one surface 101 side toward the other surface 102 side. Thereafter, by mounting the sensor chip 160 on the mounting area A, the sensor module 100F according to the fifth modification illustrated in FIG. 23 is completed.

With such a shape of the through hole V1, even when a misalignment occurs at the time of mounting of the sensor module 100F onto the motherboard 200, it is possible to ensure overlap between the through hole V1 of the sensor module 100F and the through hole V2 of the motherboard 200 and to achieve high-density mounting of the sensor chip 160. Further, the through hole V1 has a so-called megaphone structure, so that when the sensor chip 160 is a microphone, transmission characteristics of acoustic waves can be improved.

Figure 24:
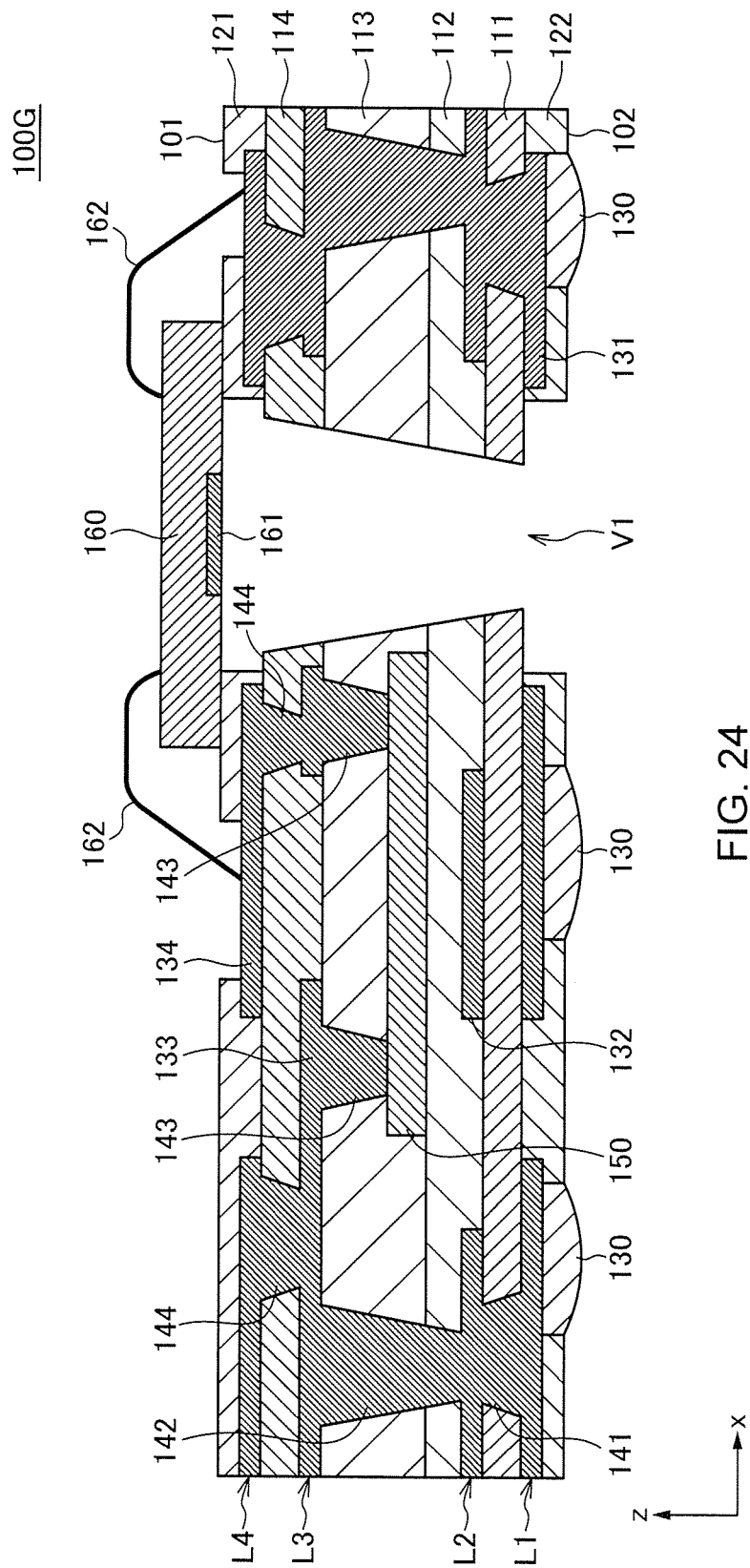
FIG. 24 is a schematic cross-sectional view for explaining the structure of a sensor module 100G according to a sixth modification.

Conversely, when laser processing or blasting is applied to only the one surface 101 side, it is possible to continuously increase the diameter of the through hole V1 from the other surface 102 side toward the one surface 101 side. Thereafter, by mounting the sensor chip 160 on the mounting area A, a sensor module 100G according to the sixth modification illustrated in FIG. 24 is completed. With such a shape of the through hole V1, it is possible to sufficiently ensure the diameter of the through hole V1 for the detection part 161.

Figure 25:
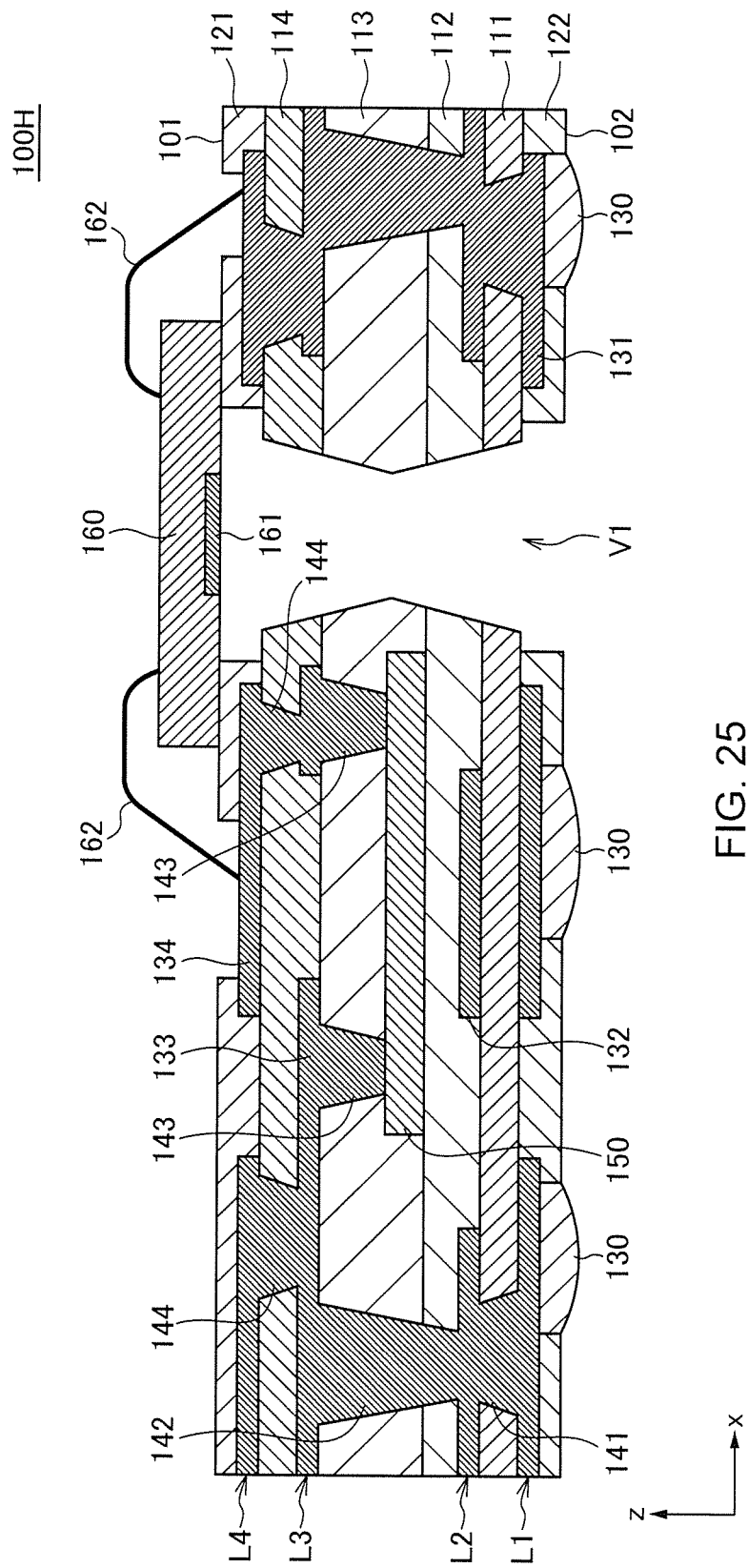
FIG. 25 is a schematic cross-sectional view for explaining the structure of a sensor module 100H according to a seventh modification.
Figure 26:
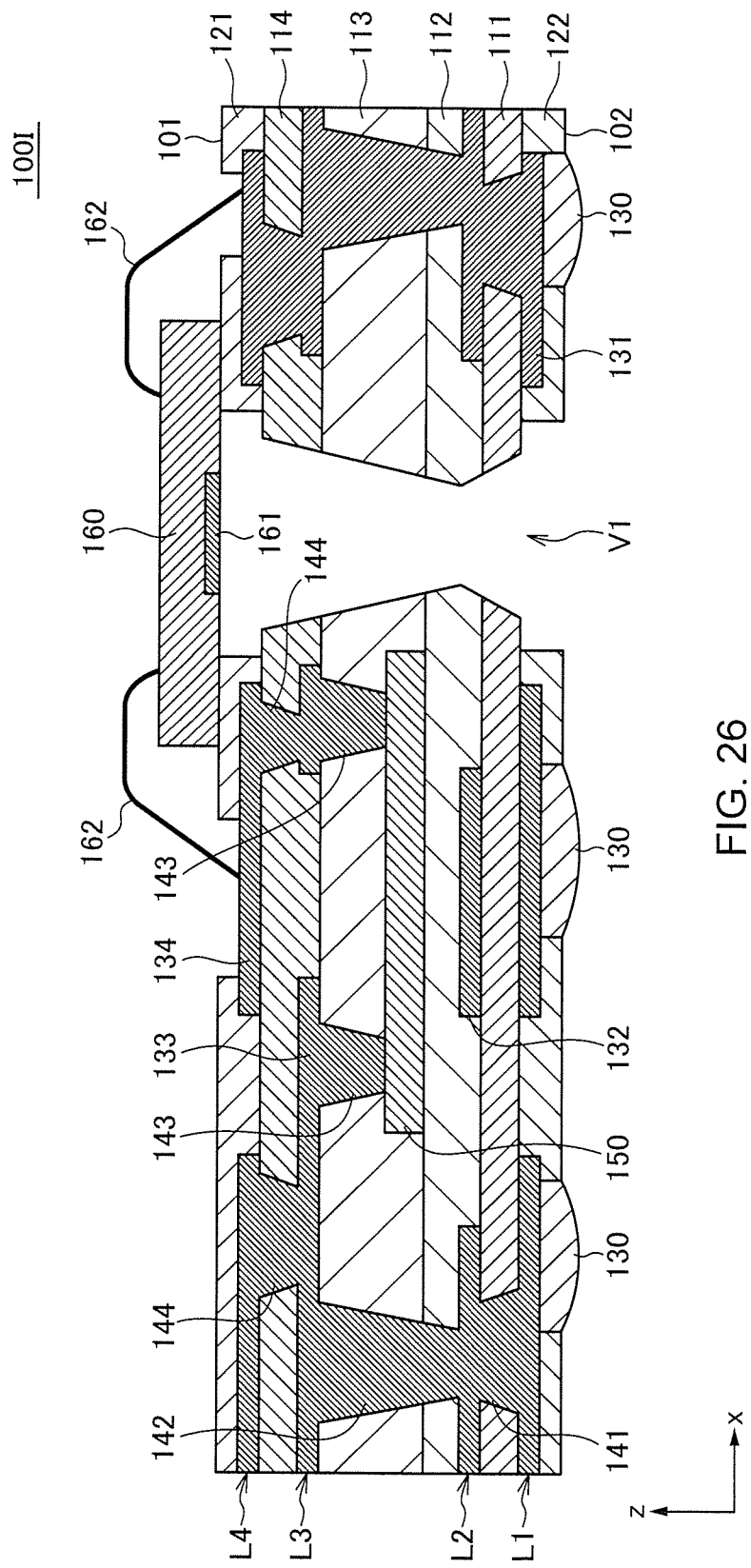
FIG. 26 is a schematic cross-sectional view for explaining the structure of a sensor module 100I according to an eighth modification.
Figure 27:
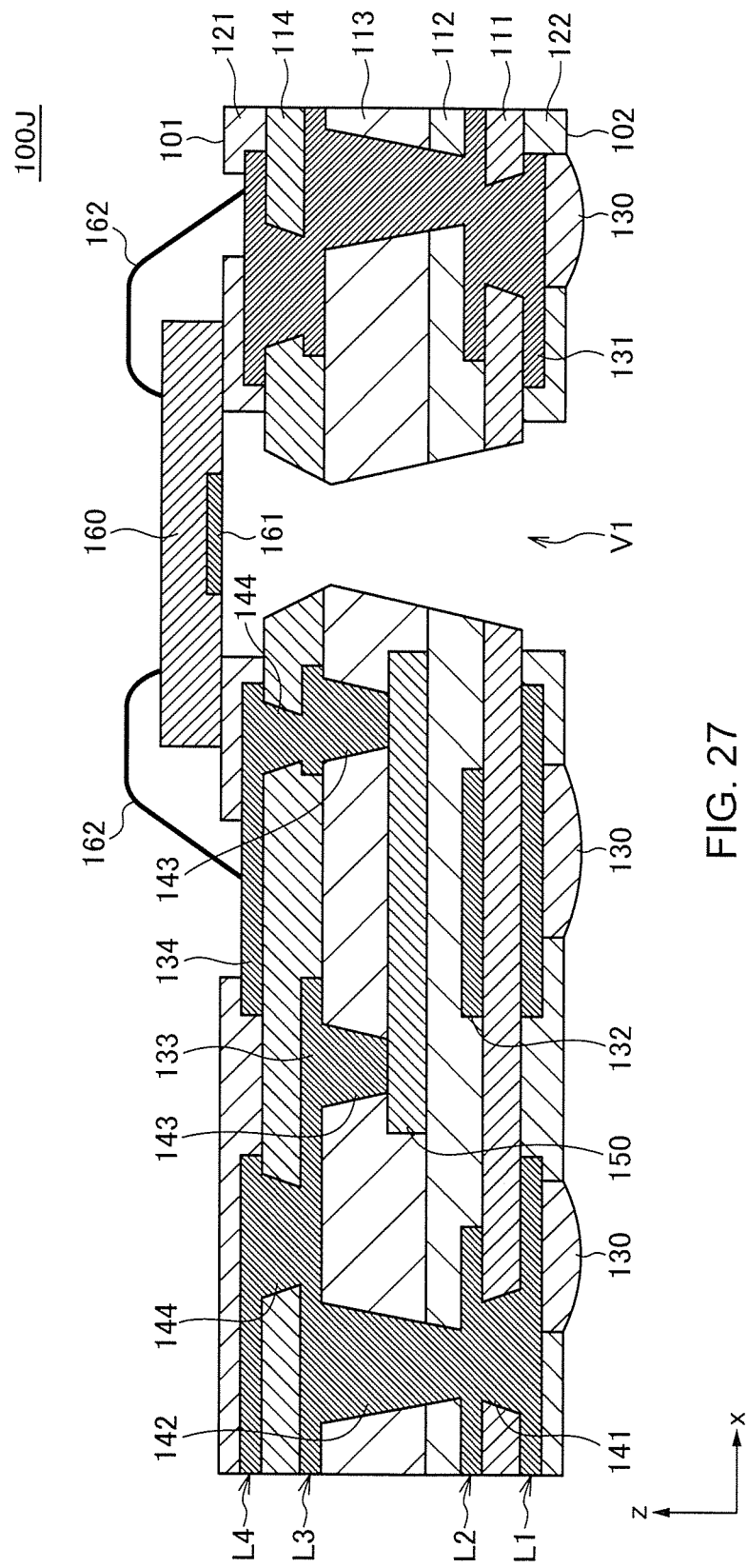
FIG. 27 is a schematic cross-sectional view for explaining the structure of a sensor module 100J according to a ninth modification.

When laser processing or blasting is applied to the front and back sides, the through hole V1 can be formed into a constricted shape like a sensor module 100H according to the seventh modification illustrated in FIG. 25. With such a shape of the through hole V1, it is possible to increase the diameter of the through hole V1 at the edges thereof on the one surface 101 side and the other surface 102 side while sufficiently ensuring a margin between the controller chip 150 and the through hole V1. In this case, the position at which the diameter of the through hole V1 is smallest need not be located at the center in the depth direction. That is, like a sensor module 100I according to the eighth modification illustrated in FIG. 26, the position at which the diameter of the through hole V1 is smallest may be offset to the other surface 102 side from the center in the depth direction, or like a sensor module 100J according to the ninth modification illustrated in FIG. 27, the position at which the diameter of the through hole V1 is smallest may be offset to the one surface 101 side from the center in the depth direction. Thus, it is possible to freely select the front and back side diameters of the through hole V1 formed in the sensor module considering a mounting misalignment of the sensor chip 160 or a mounting misalignment of the sensor module on the motherboard, allowing stable sensing characteristics to be obtained.

A method of machining the through hole V1 into a tapered shape is not limited to the above-mentioned laser processing or blasting, and even when drilling is used, the through hole V1 can be formed into a tapered shape depending on set conditions. For example, by actively utilizing the axial wobble of a rotating drill blade, it is possible to continuously vary the diameter of the through hole V1 in the depth direction.

Figure 28:
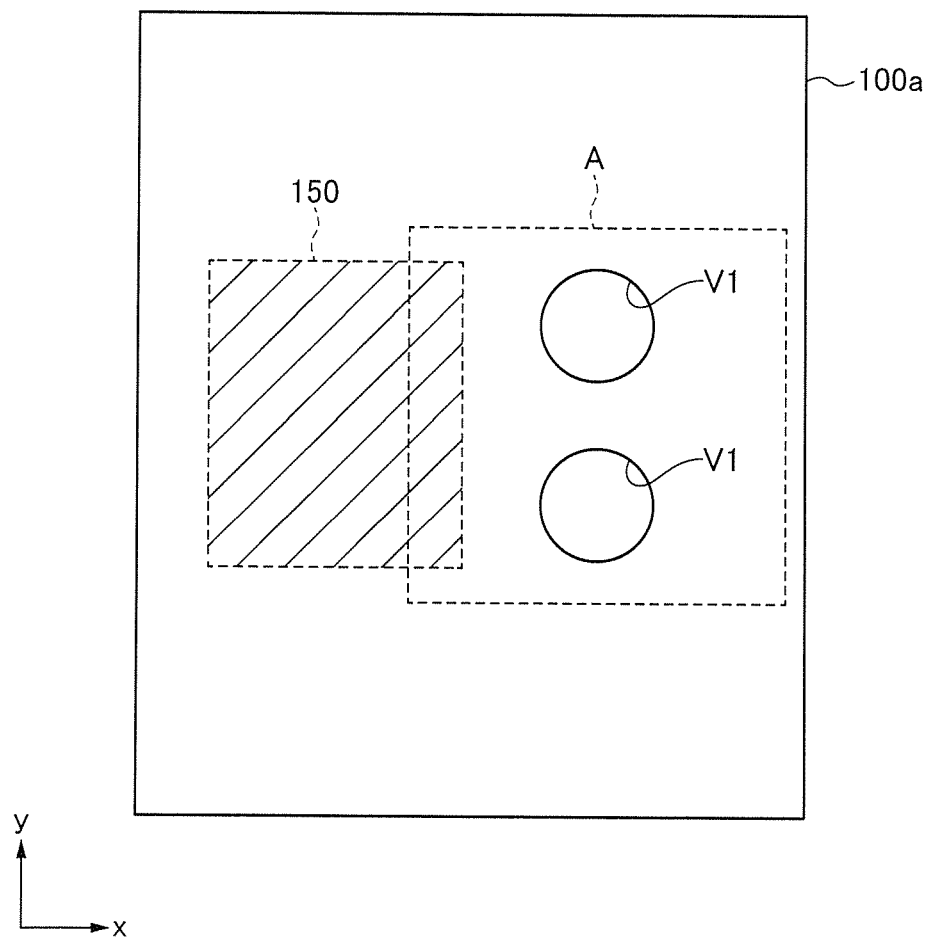
FIG. 28 is a schematic plan view for explaining the structure of a sensor package substrate 100a according a first modification.
Figure 29:
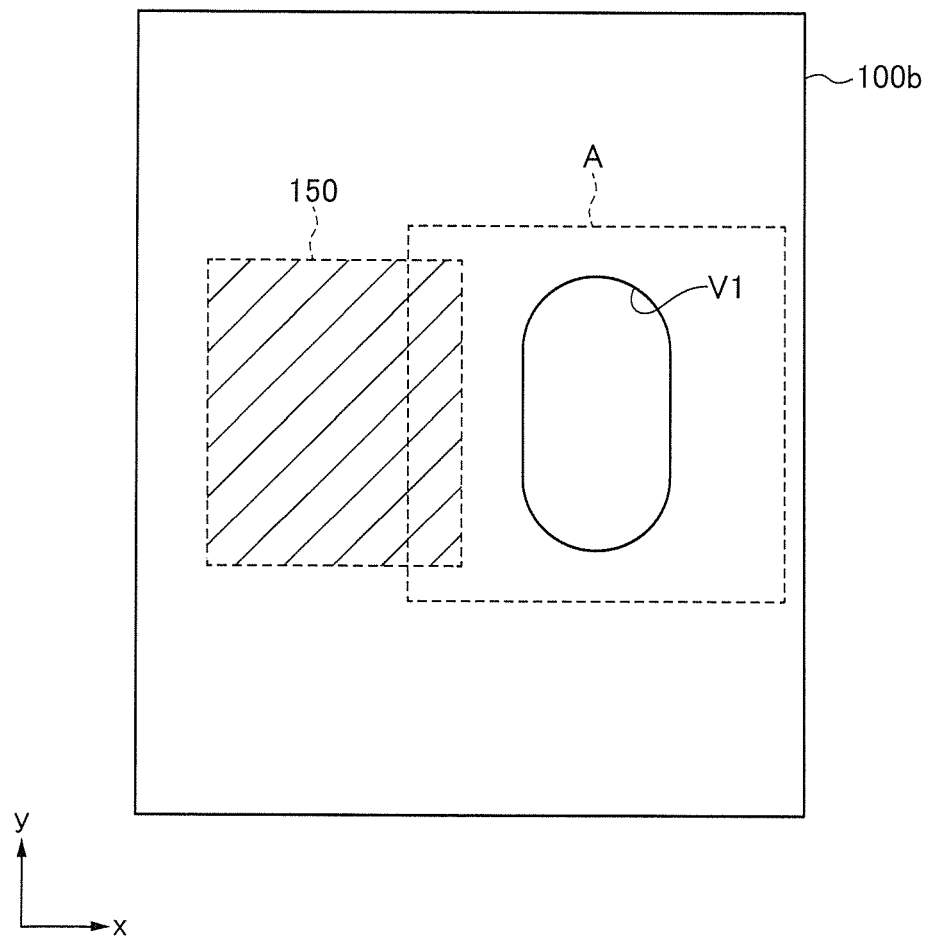
FIG. 29 is a schematic plan view for explaining the structure of a sensor package substrate 100b according a second modification.
Figure 30:
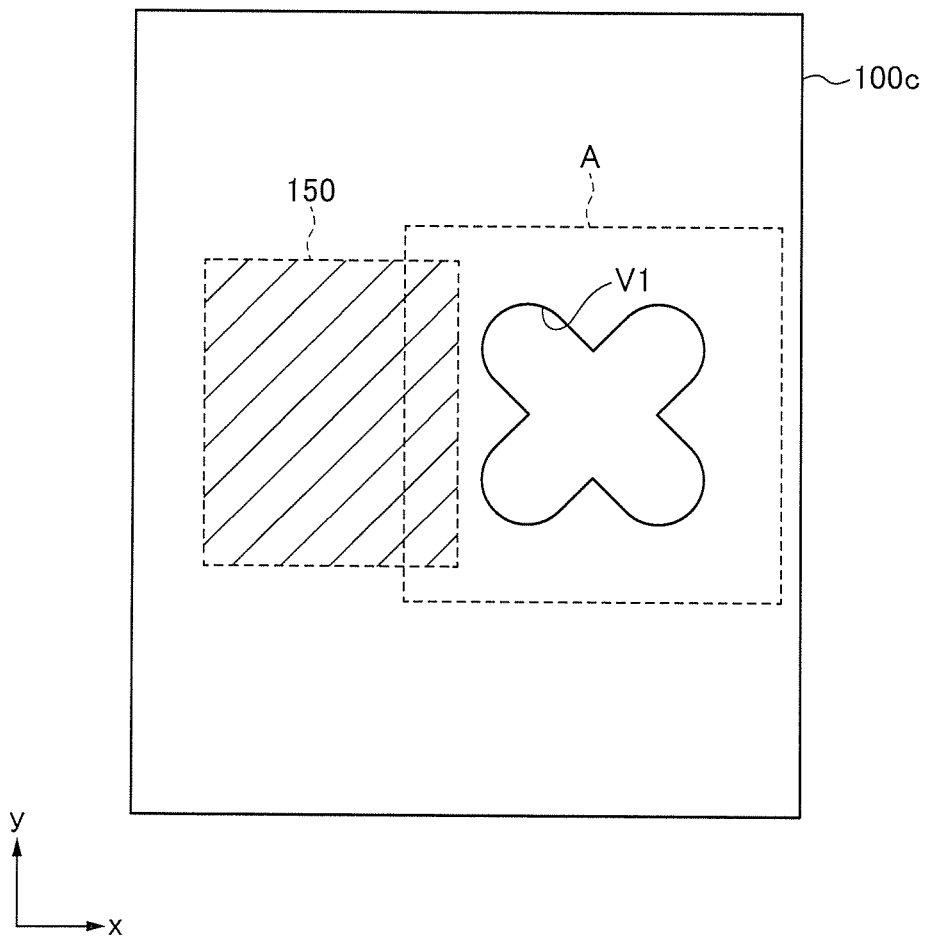
FIG. 30 is a schematic plan view for explaining the structure of a sensor package substrate 100c according a third modification.
Figure 31:
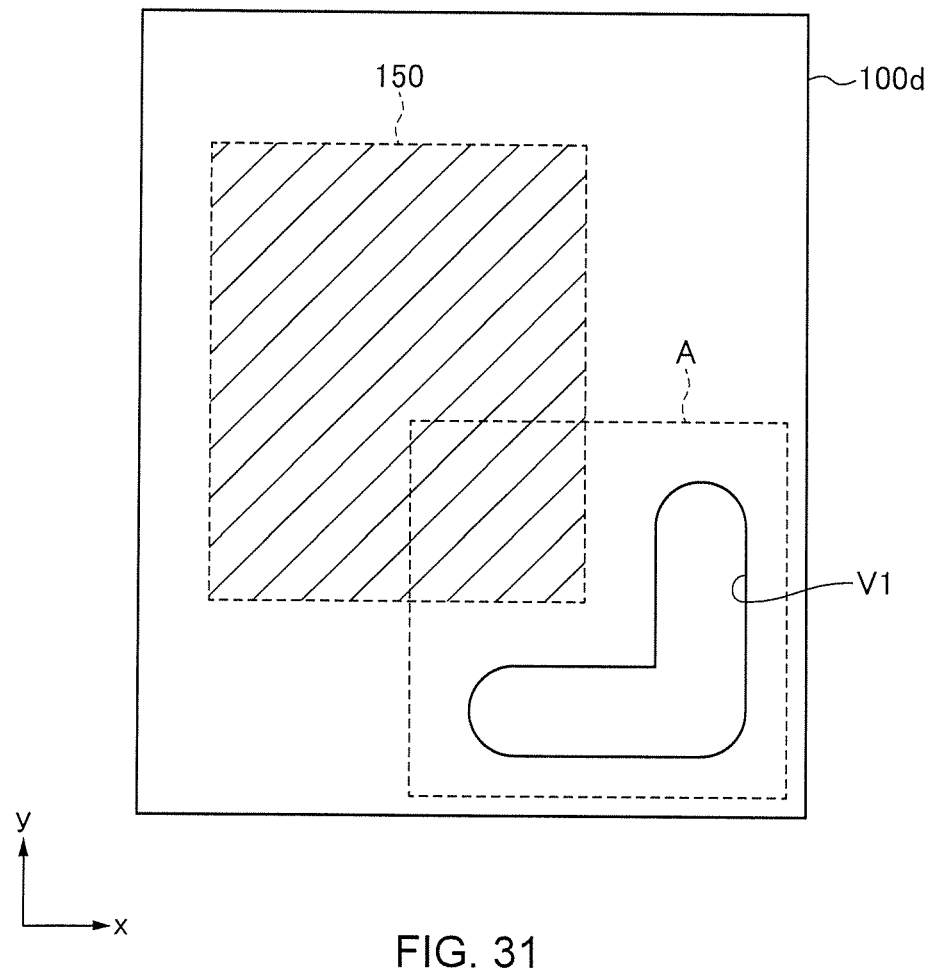
FIG. 31 is a schematic plan view for explaining the structure of a sensor package substrate 100d according a fourth modification.
Figure 32:
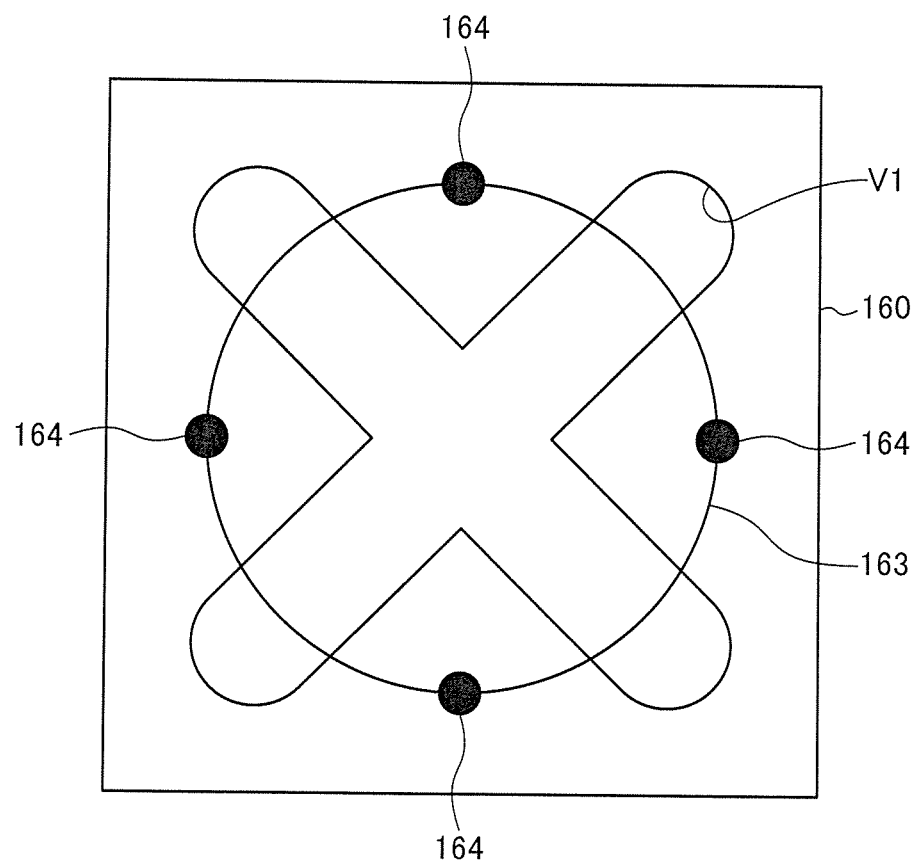
FIG. 32 is a schematic plan view for explaining one example of the relationship between a fixing part 164 of a vibration plate 163 and the through hole V1.

The number of the through holes V1 is also not particularly limited and, like a sensor package substrate 100a according to the first modification illustrated in FIG. 28, a plurality of the through holes V1 may be formed so as to overlap the mounting area A. Further, the planar shape of the through hole V1 is not limited to a circular shape, but may be a non-circular shape according to the purpose. For example, like a sensor package substrate 100*b* according to the second modification illustrated in FIG. 29, the through hole V1 may be formed into an elliptical planar shape. Alternatively, like a sensor package substrate 100*c* according to the third modification illustrated in FIG. 30, the through hole V1 may be formed into a cross planar shape, or like a sensor package substrate 100*d* according to the fourth modification illustrated in FIG. 31, the through hole V1 may be formed into an L planar shape. When the through hole V1 has across planar shape as illustrated in FIG. 32, it is positioned so as not to overlap a fixing part 164 of a vibration plate 163 provided on the sensor chip 160, whereby air vibration or the like can be transmitted efficiently to the sensor chip 160. Thus, by enabling the planar shape of the through hole V1 to be freely designed, the degree of freedom in design can be enhanced, allowing further size reduction.

Figure 33:
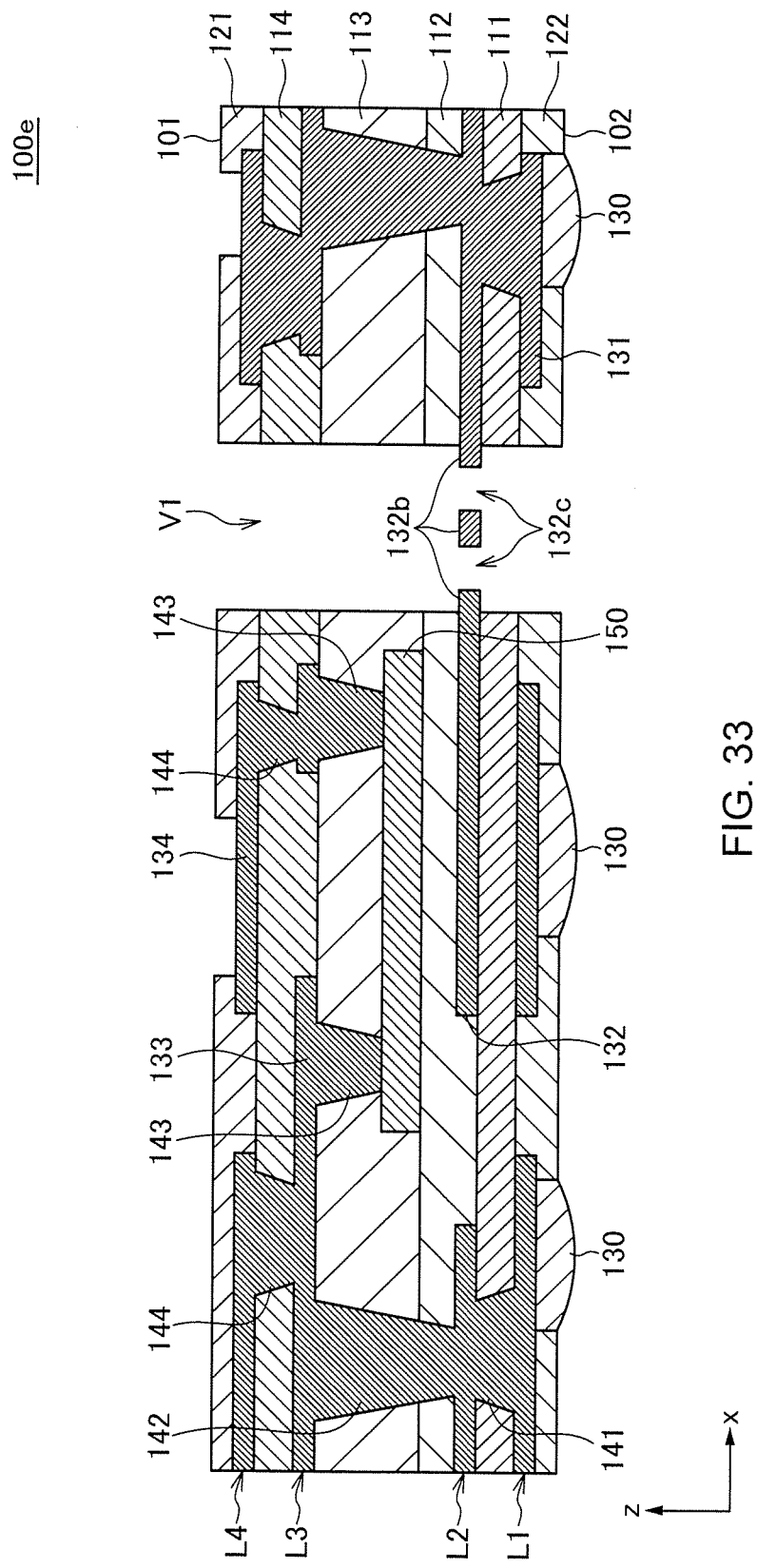
FIG. 33 is a schematic cross-sectional view for explaining the structure of a sensor package substrate 100e according a fifth modification.
Figure 34:
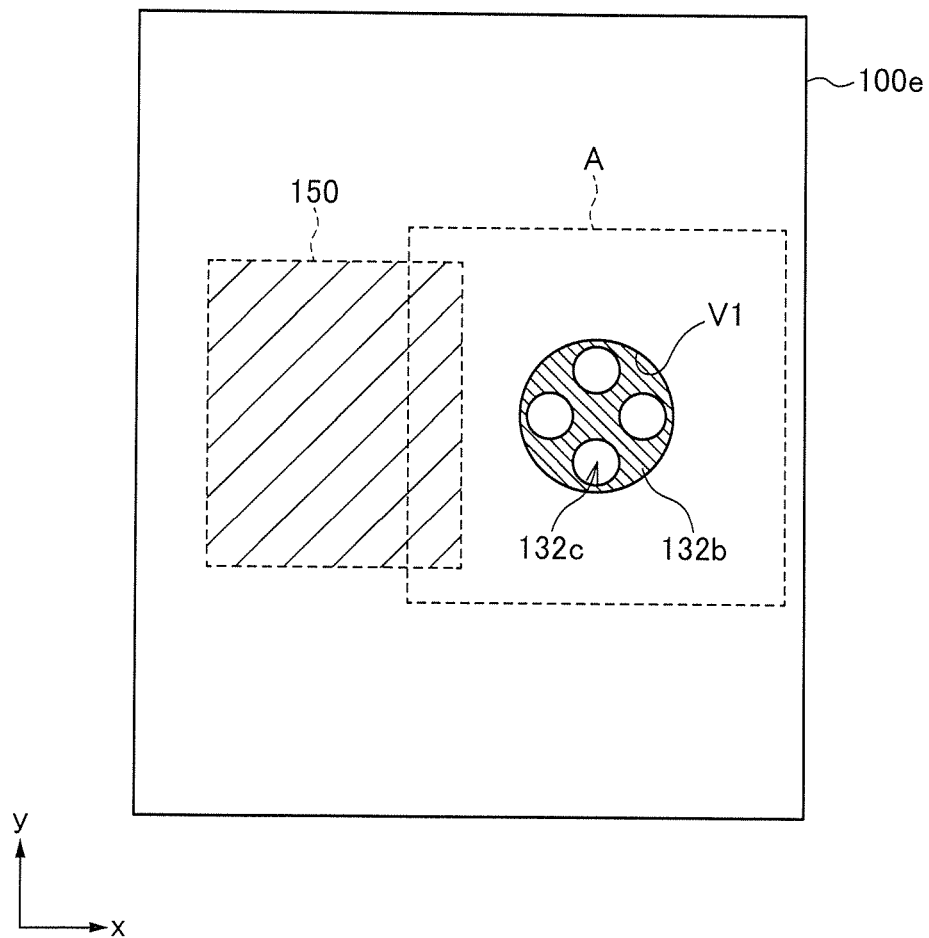
FIG. 34 is a schematic plan view for explaining the structure of the sensor package substrate 100e according the fifth modification.

FIG. 33 is a schematic cross-sectional view for explaining the structure of a sensor package substrate 100*e* according to the fifth modification. FIG. 34 is a schematic plan view of the sensor package substrate 100*e*.

The sensor package substrate 100*e* illustrated in FIGS. 33 and 34 differs from the sensor package substrate 100 illustrated in FIGS. 1 and 2 in that a metal film 132*b* constituting part of the wiring pattern 132 positioned in the wiring layer L2 exists inside the through hole V1. Other configurations are the same as those of the sensor package substrate 100 illustrated in FIGS. 1 and 2, so the same reference numerals are given to the same elements, and overlapping description will be omitted. The metal film 132*b* positioned inside the through hole V1 has a plurality of (four, in the example of FIG. 34) openings 132*c*, and an air flow is ensured through the openings 132*c*.

According to the sensor package substrate 100*e* of the present modification, when the metal film 132*b* is connected to, e.g., a ground potential, it is possible to prevent electrostatic breakdown of the sensor chip 160. In addition, dust is unlikely to adhere to the sensor chip 160 through the through hole V1. As a method of providing the metal film 132*b* inside the through hole V1, there is available a method that previously forms the metal film 132*b* having the openings 132*c* smaller in diameter than the through hole V1 and then applies later processing or blasting to the front and back sides using the method illustrated in FIGS. 18 to 20. This allows the metal film 132*b* to function as a stopper during blasting, so that it is possible to form the through hole V1 penetrating the insulating layers 111 to 114 with the metal film 132*b* left there.

Figure 35:
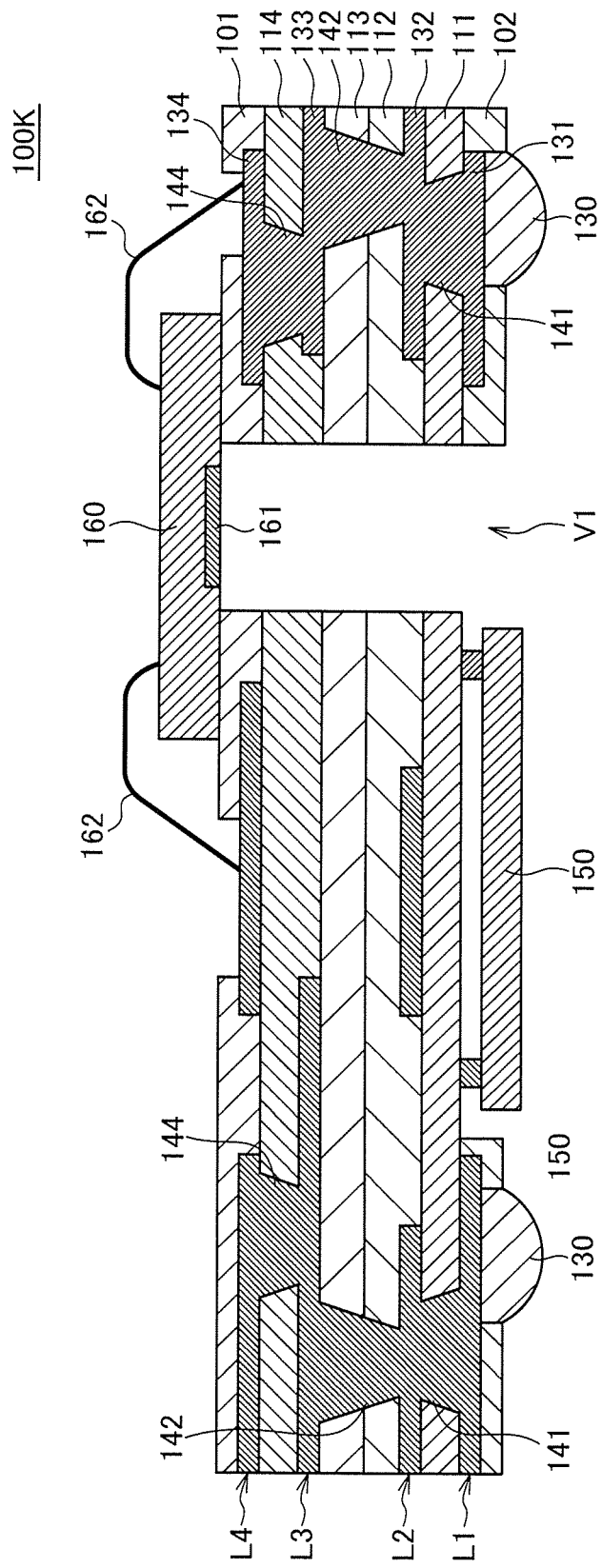
FIG. 35 is a schematic cross-sectional view for explaining the structure of a sensor module 100K according to a tenth modification.

FIG. 35 is a schematic cross-sectional view for explaining the structure of a sensor module 100K according to the tenth modification.

The sensor module 100K illustrated in FIG. 35 differs from the sensor module 100A illustrated in FIGS. 3 and 4 in that the controller chip 150 is not embedded in the substrate, but mounted on the surface of the insulating layer 111 positioned in the lowermost layer. Other configurations are the same as those of the sensor package substrate 100A illustrated in FIGS. 3 and 4, so the same reference numerals are given to the same elements, and overlapping description will be omitted. In the present modification as well, the controller chip 150 and the sensor chip 160 overlap each other in a plan view.

In the present invention, as exemplified in the present modification, the controller chip 150 may not necessarily be embedded in the substrate, but may be mounted on the surface of the substrate.

Although the present invention has been described based on the preferred embodiments, the present invention is not limited to the above embodiments and various modifications may be made within the scope of the present invention, and and all such modifications may be included within the scope of the present invention.

What is claimed is:

1. A sensor package substrate comprising:
   a mounting area which is provided on one surface thereof for mounting a sensor chip; and
   an electronic component connected to the sensor chip,
   wherein a through hole is formed in the sensor package substrate so as to overlap the mounting area in a plan view and to penetrate the sensor package substrate from the one surface to another surface thereof,
   wherein the mounting area and the electronic component overlap each other in a plan view,
   wherein the through hole has a first section positioned at a side of the one surface and a second section positioned at a side of the another surface, and a third section positioned between the first and second sections,
   wherein a center axis of the first section of the through hole is offset from a center axis of the second section of the through hole,
   wherein a diameter of the first section of the through hole is a same as a diameter of the second section of the through hole,
   wherein the sensor package substrate has a configuration in which a plurality of insulating layers are stacked on one another,
   wherein the plurality of insulating layers includes a first insulating layer containing a core material and a second insulating layer not containing a core material, and
   wherein the third section of the through hole is positioned at the second insulating layer so as not to expose the core material from an inner wall of the through hole at the third section.

2. The sensor package substrate as claimed in claim 1, wherein a diameter of the third section of the through hole is greater than the diameter of the first section of the through hole.

3. The sensor package substrate as claimed in claim 2, wherein the first section of the through hole is a section closest to the side of the one surface.

4. The sensor package substrate as claimed in claim 3, wherein the second section of the through hole is a section closest to the side of the another surface.

5. The sensor package substrate as claimed in claim 4, wherein the third section of the through hole is shorter than each of the first and second sections of the through hole.

6. The sensor package substrate as claimed in claim 1,
   wherein the electronic component is embedded in the sensor package substrate, and
   wherein a depth position of the electronic component overlaps a depth position of the third section of the through hole.

7. The sensor package substrate as claimed in claim 1, further comprising the sensor chip mounted on the mounting area,
   wherein the sensor chip is a sensor that detects air vibration, air pressure, air temperature or air composition.

8. A sensor package substrate comprising:
a substrate having a first surface and a second surface positioned opposite to the first surface; and
an electronic component embedded in the substrate,
wherein the substrate has a through hole penetrating the substrate from the first surface to the second surface,
wherein the through hole has a first section positioned at a first surface side of the through hole, a second section positioned at a second surface side of the through hole, and a third section positioned between the first and second sections,
wherein a diameter of each of the first and second sections is substantially constant in a depth direction, and
wherein the third section has a tapered shape in which a diameter thereof continuously varies in the depth direction,
wherein the first section of the through hole is a section closest to the side of the first surface,
wherein the second section of the through hole is a section closest to the side of the second surface,
wherein the third section of the through hole is longer than each of the first and second sections of the through hole, and
wherein the diameter of the third section at a first end connected to the first section is smaller than the diameter of the first section.

9. The sensor package substrate as claimed in claim 8, wherein the diameter of the third section at a second end connected to the second section is smaller than the diameter of the second section.

10. The sensor package substrate as claimed in claim 9, wherein the diameter of the first section is smaller than the diameter of the second section.

11. The sensor package substrate as claimed in claim 8, further comprising a sensor chip mounted on the first surface of the substrate so as to overlap the through hole,
wherein the sensor chip is connected to the electronic component.

12. A sensor package substrate comprising:
a substrate having a first surface and a second surface positioned opposite to the first surface; and
an electronic component embedded in the substrate,
wherein the substrate has a through hole penetrating the substrate from the first surface to the second surface,
wherein the through hole has a first section positioned at a side of the first surface and surrounded by a first inner wall of the substrate, a second section positioned at a side of the second surface and surrounded by a second inner wall of the substrate, and a third section positioned between the first and second sections and surrounded by a part of the first inner wall and a part of the second inner wall,
wherein the substrate has a configuration in which a plurality of insulating layers are stacked on one another,
wherein the plurality of insulating layers includes a first insulating layer containing a core material and a second insulating layer not containing a core material, and
wherein the third section of the through hole is positioned at the second insulating layer so as not to expose the core material from the first and second inner walls at the third section.

13. The sensor package substrate as claimed in claim 12,
wherein a center axis of the first section of the through hole is offset from a center axis of the second section of the through hole, and
wherein a diameter of the first section of the through hole is a same as a diameter of the second section of the through hole.

14. The sensor package substrate as claimed in claim 13,
wherein the first section of the through hole is a section closest to the side of the first surface, and
wherein the second section of the through hole is a section closest to the side of the second surface.

15. The sensor package substrate as claimed in claim 14,
wherein a depth position of the electronic component overlaps a depth position of the third section of the through hole.

16. The sensor package substrate as claimed in claim 12,
further comprising a sensor chip mounted on the first surface of the substrate so as to overlap the through hole,
wherein the sensor chip is connected to the electronic component.

* * * * *